(12) United States Patent
Lamborne et al.

(10) Patent No.: US 10,667,927 B2
(45) Date of Patent: Jun. 2, 2020

(54) EXPANDABLE FUSION CAGE SYSTEM

(71) Applicant: IN QUEUE INNOVATIONS, LLC, Winona Lake, IN (US)

(72) Inventors: Andrew Lamborne, Golden, CO (US); Patrick Hunt, Broomfield, CO (US); Joel Helgerson, Broomfield, CO (US); Troy Woolley, Broomfield, CO (US); Richard Fessler, Winnetka, IL (US); Clint Hill, Broomfield, CO (US); K. Brandon Strenge, Broomfield, CO (US); Kenneth Little, Broomfield, CO (US); Alex Speciale, Broomfield, CO (US)

(73) Assignee: IN QUEUE INNOVATIONS, LLC, Winona Lake, IN (US)

( * ) Notice: Subject to any disclaimer, the term of this patent is extended or adjusted under 35 U.S.C. 154(b) by 101 days.

(21) Appl. No.: 16/056,096

(22) Filed: Aug. 6, 2018

(65) Prior Publication Data
US 2019/0008657 A1 Jan. 10, 2019

Related U.S. Application Data

(63) Continuation of application No. 14/774,038, filed as application No. PCT/US2014/029214 on Mar. 14, 2014, now Pat. No. 10,039,650.
(Continued)

(51) Int. Cl.
*A61F 2/46* (2006.01)
*A61F 2/44* (2006.01)
(Continued)

(52) U.S. Cl.
CPC .......... *A61F 2/4611* (2013.01); *A61F 2/447* (2013.01); *A61F 2/4425* (2013.01);
(Continued)

(58) Field of Classification Search
CPC ........ A61F 2/4455; A61F 2/446; A61F 2/447; A61F 2002/4475; A61F 2/4611; A61F 2/4425; A61F 2002/30266
See application file for complete search history.

(56) References Cited

U.S. PATENT DOCUMENTS

| 5,059,193 A | 10/1991 | Kuslich |
| 5,554,191 A | 9/1996 | Lahille |
| (Continued) | | |

FOREIGN PATENT DOCUMENTS

| DE | 102012023042 | 11/2012 |
| DE | 102013102955 | 10/2014 |
| (Continued) | | |

OTHER PUBLICATIONS

International Search Report and Written Opinion of the International Searching Authority for PCT/US2014/029214, dated Aug. 5, 2014, 19 pages.
(Continued)

*Primary Examiner* — Matthew J Lawson
(74) *Attorney, Agent, or Firm* — Heslin Rothenberg Farley & Mesiti P.C.

(57) ABSTRACT

An expandable fusion cage system includes an expandable fusion cage having an upper portion, a lower portion, and a hinge portion coupling the lower portion and the upper portion at their distal ends. Positioned between the upper and lower portions is an expansion element that when moved in the proximal direction causes the cage to expand at its proximal end. The system can also include inserter instruments, expandable distraction instruments, and bone funnels.

20 Claims, 40 Drawing Sheets

US 10,667,927 B2

Page 2

Related U.S. Application Data

(60) Provisional application No. 61/799,412, filed on Mar. 15, 2013.

(51) Int. Cl.
*A61F 2/30* (2006.01)
*A61B 17/02* (2006.01)

(52) U.S. Cl.
CPC .... *A61F 2/4455* (2013.01); *A61B 2017/0256* (2013.01); *A61F 2/4603* (2013.01); *A61F 2002/30261* (2013.01); *A61F 2002/30266* (2013.01); *A61F 2002/30331* (2013.01); *A61F 2002/30398* (2013.01); *A61F 2002/30471* (2013.01); *A61F 2002/30538* (2013.01); *A61F 2002/30556* (2013.01); *A61F 2002/30579* (2013.01); *A61F 2002/30774* (2013.01); *A61F 2002/30777* (2013.01); *A61F 2002/30797* (2013.01); *A61F 2002/30904* (2013.01); *A61F 2002/4627* (2013.01); *A61F 2250/0058* (2013.01)

(56) References Cited

U.S. PATENT DOCUMENTS

| | | | |
|---|---|---|---|
| 5,665,122 A | 9/1997 | Kambin | |
| 6,117,174 A | 9/2000 | Nolan | |
| 6,129,763 A | 10/2000 | Chauvin | |
| 6,368,351 B1 | 4/2002 | Glenn | |
| 6,371,989 B1 | 4/2002 | Chauvin | |
| 6,395,031 B1 | 5/2002 | Foley | |
| 6,436,140 B1 | 8/2002 | Liu | |
| 6,436,142 B1 | 8/2002 | Paes | |
| 6,443,989 B1 | 9/2002 | Jackson | |
| 6,454,807 B1 | 9/2002 | Jackson | |
| 6,491,724 B1 | 12/2002 | Ferree | |
| 6,562,074 B2 | 5/2003 | Gerbec | |
| 6,648,917 B2 | 11/2003 | Gerbec | |
| 6,656,178 B1 | 12/2003 | Veldhuizen | |
| 6,666,891 B2 | 12/2003 | Boehm, Jr. | |
| 6,685,742 B1 | 2/2004 | Jackson | |
| 6,730,126 B2 | 5/2004 | Boehm, Jr. | |
| 6,743,255 B2 | 6/2004 | Ferree | |
| 6,773,460 B2 | 8/2004 | Jackson | |
| 6,821,298 B1 | 11/2004 | Jackson | |
| 6,835,206 B2 | 12/2004 | Jackson | |
| 6,852,129 B2 | 2/2005 | Gerbec | |
| 6,863,673 B2 | 3/2005 | Gerbec | |
| 6,875,213 B2 | 4/2005 | Michelson | |
| 6,905,512 B2 | 6/2005 | Paes | |
| 6,955,691 B2 | 10/2005 | Chae | |
| 7,008,453 B1 | 3/2006 | Michelson | |
| 7,018,415 B1 | 3/2006 | McKay | |
| 7,128,760 B2 | 10/2006 | Michelson | |
| 7,211,112 B2 | 5/2007 | Baynham | |
| 7,217,293 B2 | 5/2007 | Branch, Jr. | |
| 7,220,280 B2 | 5/2007 | Kast | |
| 7,410,501 B2 | 8/2008 | Michelson | |
| 7,431,735 B2 | 10/2008 | Liu | |
| 7,445,636 B2 | 11/2008 | Michelson | |
| 7,655,027 B2 | 2/2010 | Michelson | |
| 7,655,046 B2 | 2/2010 | Dryer | |
| 7,678,148 B2 | 3/2010 | Peterman | |
| 7,727,280 B2 | 6/2010 | McLuen | |
| 7,828,848 B2 | 11/2010 | Chauvin | |
| 7,850,733 B2 | 12/2010 | Baynham | |
| 7,875,078 B2 | 1/2011 | Wysocki | |
| 7,879,098 B1* | 2/2011 | Simmons, Jr. | A61F 2/4465 623/17.11 |
| 7,993,403 B2 | 8/2011 | Foley | |
| 8,080,041 B2 | 12/2011 | Boehm, Jr. | |
| D664,252 S | 7/2012 | Weiland | |
| 8,221,502 B2 | 7/2012 | Branch, Jr. | |
| 8,267,939 B2 | 9/2012 | Cipoletti | |
| 8,273,129 B2 | 9/2012 | Baynham | |
| 8,303,658 B2 | 11/2012 | Peterman | |
| 8,333,804 B1 | 12/2012 | Wensel | |
| 8,349,014 B2 | 1/2013 | Barreiro | |
| 8,403,990 B2 | 3/2013 | Dryer | |
| 8,435,299 B2 | 5/2013 | Chauvin | |
| 8,460,385 B1 | 6/2013 | Wensel | |
| 8,623,088 B1* | 1/2014 | Tohmeh | A61F 2/4455 623/17.11 |
| 8,641,767 B2 | 2/2014 | Landry | |
| 9,259,328 B2* | 2/2016 | Pabst | A61F 2/442 |
| 9,662,224 B2 | 5/2017 | Weiman et al. | |
| 9,801,734 B1* | 10/2017 | Stein | A61F 2/447 |
| 10,555,818 B2* | 2/2020 | McConnell | A61F 2/4684 |
| 2002/0068977 A1 | 6/2002 | Jackson | |
| 2002/0161444 A1 | 10/2002 | Choi | |
| 2004/0127994 A1 | 7/2004 | Kast | |
| 2005/0021041 A1 | 1/2005 | Michelson | |
| 2005/0113916 A1* | 5/2005 | Branch, Jr. | A61F 2/447 623/17.11 |
| 2005/0283248 A1 | 12/2005 | Gordon | |
| 2006/0167547 A1* | 7/2006 | Suddaby | A61F 2/446 623/17.11 |
| 2008/0140207 A1 | 6/2008 | Olmos | |
| 2010/0185291 A1 | 7/2010 | Jimenez | |
| 2010/0234956 A1 | 9/2010 | Attia | |
| 2010/0286780 A1 | 11/2010 | Dryer | |
| 2011/0172277 A1 | 7/2011 | Bradford | |
| 2011/0172774 A1 | 7/2011 | Varela | |
| 2011/0224796 A1 | 9/2011 | Weiland | |
| 2012/0083887 A1 | 4/2012 | Purcell | |
| 2012/0271422 A1 | 10/2012 | Miller | |
| 2013/0158664 A1 | 6/2013 | Palmatier | |
| 2013/0166030 A1 | 6/2013 | Biedermann et al. | |
| 2013/0310941 A1 | 11/2013 | Chauvin | |
| 2014/0156007 A1 | 6/2014 | Pabst et al. | |
| 2014/0249628 A1 | 9/2014 | Weiman | |
| 2014/0257486 A1 | 9/2014 | Alheidt | |
| 2014/0277484 A1 | 9/2014 | Prevost et al. | |
| 2015/0100126 A1 | 4/2015 | Melkent et al. | |
| 2015/0328008 A1 | 11/2015 | Fessler | |
| 2015/0351925 A1 | 12/2015 | Emerick et al. | |
| 2016/0310294 A1 | 10/2016 | McConnell et al. | |
| 2020/0100904 A1* | 4/2020 | Stein | A61F 2/447 |

FOREIGN PATENT DOCUMENTS

| | | |
|---|---|---|
| EP | 1382315 | 1/2004 |
| EP | 1415623 | 5/2004 |
| FR | 2866229 | 8/2005 |
| WO | 2014144696 | 9/2014 |
| WO | 2017051416 | 3/2017 |

OTHER PUBLICATIONS

International Preliminary Report on Patentability for PCT/US2014/029214, dated Sep. 15, 2015, 11 pages.
Extended European Search Report for EP Application No. 14764054.4, dated Sep. 20, 2016, 7 pages.

* cited by examiner

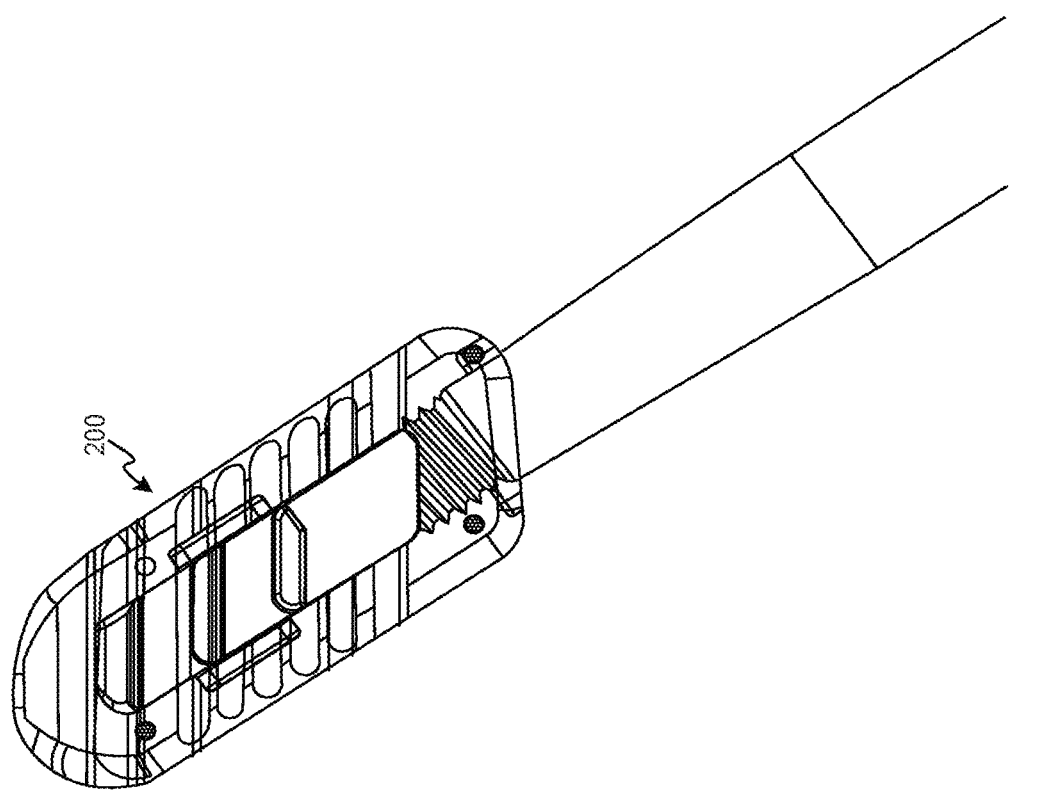

EXPANDABLE FUSION CAGE SYSTEM

CROSS REFERENCE TO RELATED APPLICATIONS

This application is a continuation of U.S. application Ser. No. 14/774,038 filed Sep. 9, 2015, which will issue as U.S. Pat. No. 10,039,650 on Aug. 7, 2018, which is a U.S. National Stage Filing under 35 U.S.C. § 371 from International Application No. PCT/US2014/029214 filed on Mar. 14, 2014, and published as WO 2014/144696 on Sep. 18, 2014, which claims priority benefit under 35 U.S.C. § 119(e) of U.S. Provisional Application No. 61/799,412 filed Mar. 15, 2013, which applications are incorporated herein by reference in their entireties.

BACKGROUND OF THE INVENTION

When posterior interbody fusion is performed (such as TLIF, OLIF or PLIF technique), it is difficult to insert a large enough fusion cage through the posterior access, especially when the disc space is significantly taller anteriorly than posteriorly. Limiting factors include the maximum height and width of the posterior access to the disc space, as well as the risk of injuring the nerve roots or thecal sac that are immediately adjacent to the pathway of access to the disc. It is not uncommon for a posteriorly inserted fusion cage to fit reasonably tightly (appropriately sized) within the posterior portion of the disc space, but to be loose (undersized) with respect to the anterior portion of the disc space. The inability to insert a properly sized fusion cage may prevent the surgeon from obtaining as much lordosis in the fused segment as desired, and may also increase the risk of post-operative migration or retropulsion of the cage. Both situations may result in reduced efficacy of the surgical treatment.

Attempting to insert a larger fusion cage than the anatomical limitations of the posterior access allow (in an attempt to avoid the problems associated with an undersized cage) may cause a number of complications such as fracture of the vertebral endplates (which may increase the risk of implant subsidence), over-stretching of the nerve roots (which may result in temporary or permanent neurologic complications), "nicking" the nerve root or dura (which may result in CSF leakage or other neurologic complications), or fracturing the implant due to overly aggressive impaction.

Other surgical approaches to the disc space (such as an ALIF or lateral transpsoas approach) help alleviate some or all of the problems identified above, but may have other drawbacks. The most commonly used approach for interbody spinal fusion is the posterior approach, thus the other potential problems with these alternative surgical approaches often outweigh the problem associated with the posterior access.

Some interbody fusion cages are designed to be inserted into the disc space on their sides, then rotated ninety degrees (90°) into the final position once inside the disc space. This allows an implant that is tall but narrow to be inserted with less cephalad-caudal distraction of the anatomy during insertion. However, the tradeoff is that the medial-lateral width of these cages is larger during insertion. Especially in the case of very tall cages (such as a cage with a high degree of lordosis), the anatomy may not accommodate the required cage height when it is turned on its side for insertion. These "insert and rotate" cages are also associated with other potential complications such as inability to rotate the cage into final position (this rotation requires some over-distraction of the disc space, which may not always be desirable or achievable), or fracture of the cage due to the twisting forces required to rotate the cage into position.

Other interbody fusion cages solve the problem by providing for expansion of the implant after it is placed into the disc space. The existing art demonstrates a number of different designs for achieving this, each of which has its own pros and cons.

SUMMARY OF THE INVENTION

The present disclosure is directed to spinal implants that are expandable to provide adjustable lordosis, and surgical instruments for use with the implants. This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

These and other aspects of the present system and method will be apparent after consideration of the Detailed Description and Figures herein.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified.

FIGS. 21A through 27 are various partial see-through top view of an expandable fusion cage according to various embodiments described herein;

DETAILED DESCRIPTION FOR CARRYING OUT THE INVENTION

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense. Moreover, the technology of the present application will be described with relation to exemplary embodiments. The word "exemplary" is used herein to mean "serving as an example, instance, or illustration." Any embodiment described herein as "exemplary" is not necessarily to be construed as preferred or advantageous over other embodiments. Additionally, unless specifically identified otherwise, all embodiments described herein should be considered exemplary.

Expandable lumber interbody fusion (ELTF) cages, such as those disclosed herein, solve one or more of the above problems by providing the ability to expand the cage to the desired anterior height. Because the posterior end of the cage does not increase in height, this expansion increases the lordosis of the cage. Expansion of the cage is achieved by pushing a wedge-like slider anteriorly, such that it wedges the anterior end of the cage apart.

With reference to figures IA through 20, the expandable fusion cage (or spinal implant) 100 can include an upper portion 110, a lower portion 120, a hinge portion 130, and expansion element 140.

Figure 1A:
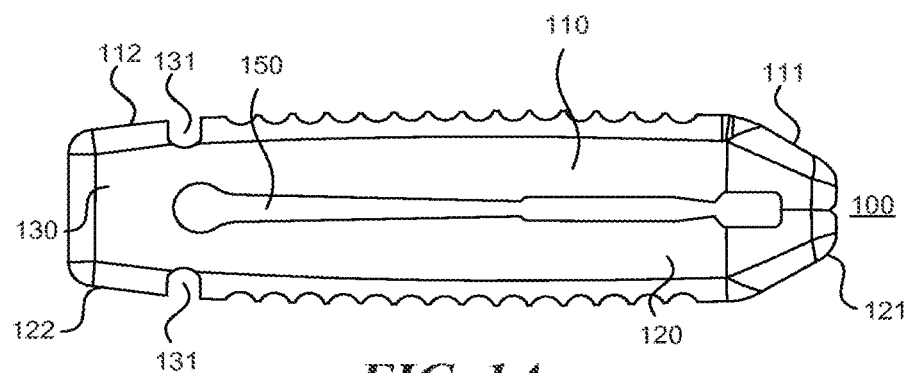
FIGS. 1A-1C are a side, front end, and back end view, respectively, of an expandable fusion cage according to various embodiments described herein.
Figure 1B:
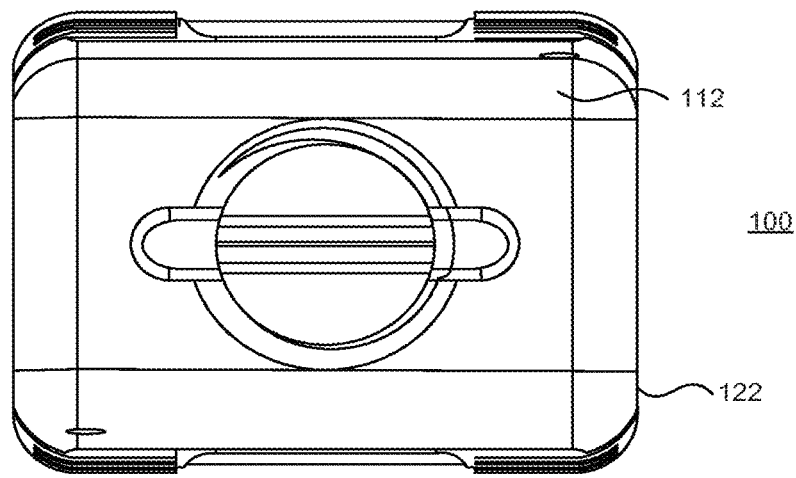
Figure 1C:
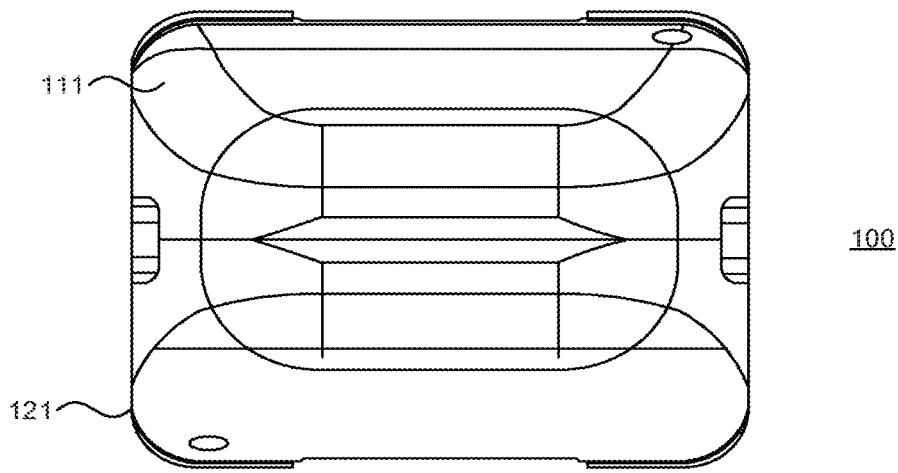
Figure 2A:
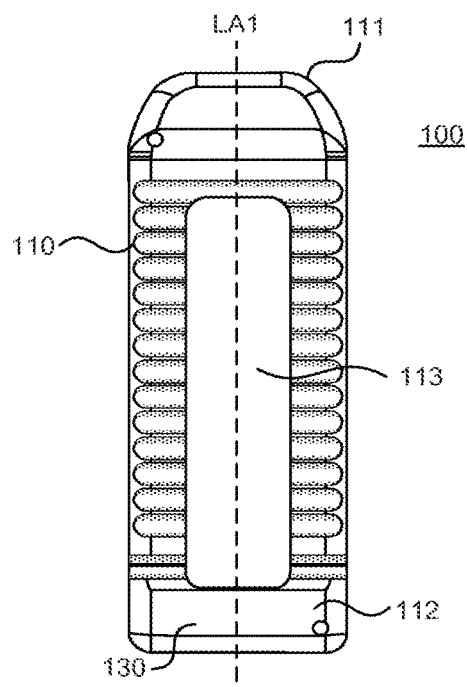
FIGS. 2A-2C are a top, perspective, and side view, respectively, of an expandable fusion cage according to various embodiments described herein.
Figure 2B:
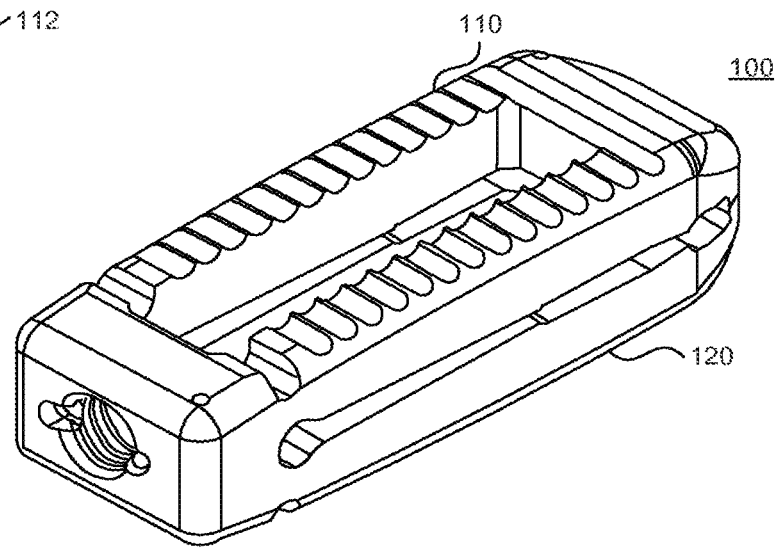
Figure 2C:
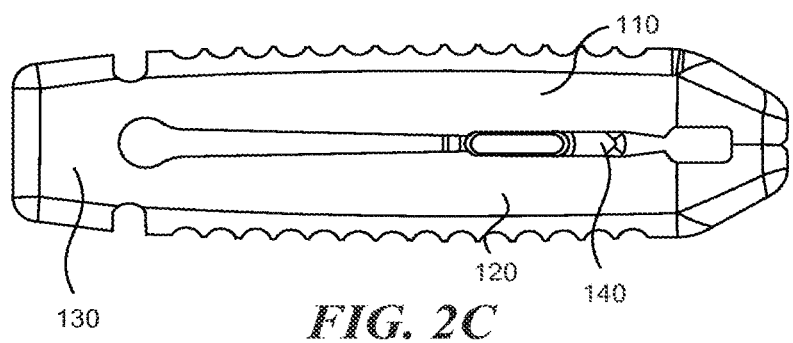

The upper portion 110 can include proximal end 111, a distal end 112, and a longitudinal axis LA1 extending therebetween. The upper portion 110 can further include an opening 113 (shown in, e.g., FIG. 2A). The opening 113 can extend longitudinally, and typically terminates prior to the proximal end 111 and distal end 112.

The lower portion 120 can include proximal end 121, a distal end 122, and a longitudinal axis LA1 extending therebetween. The lower portion 120 can further include an opening 123. The opening 123 can extend longitudinally, and typically terminates prior to the proximal end 121 and distal end 122. In some embodiments, the opening 113 and the opening 123 are aligned.

Each of the upper portion 110 and the lower portion 120 includes an upper (outer) surface and a lower (inner) surface opposing the upper surface. The lower surface of upper portion 110 generally faces the lower surface of the lower portion 120. The lower surfaces of the upper portion 110 and lower portion 120 are generally adapted to engaged the expansion element 140. In some embodiments, the openings 113 and 123 define a channel 150 between the upper portion 110 and lower portion 120. In some embodiments, the expansion member 140 resides within this slot 150 and can be moved distally and/or proximally within the channel 150. In some embodiments, the distance between the lower surfaces of the upper portion 110 and the lower portion 120 decreases towards the proximal end 111/121 of the spinal implant 100. In this manner, moving the expansion member 140 towards the proximal end 111/121 tends to cause the upper portion 110 and lower portion 120 to move apart at the proximal end (the distal ends of the lower 120 portion and the upper portion 110 tend to stay together because of the hinged portion 130).

Figure 3A:
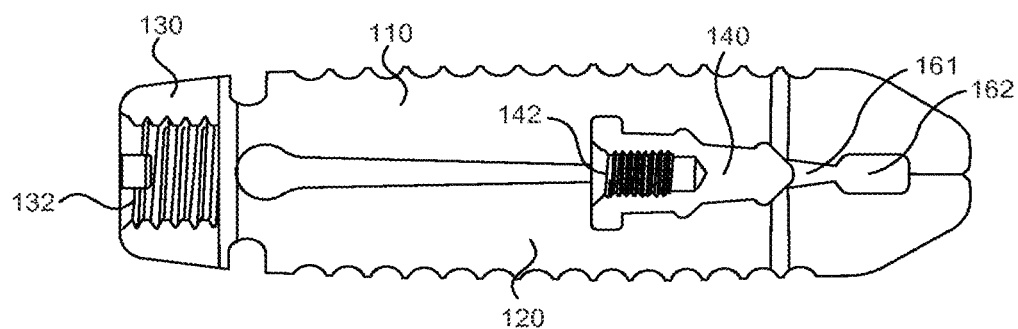
FIGS. 3A-3C are a side cross sectional, top, and perspective view, respectively, of an expandable fusion cage according to various embodiments described herein.
Figure 3B:
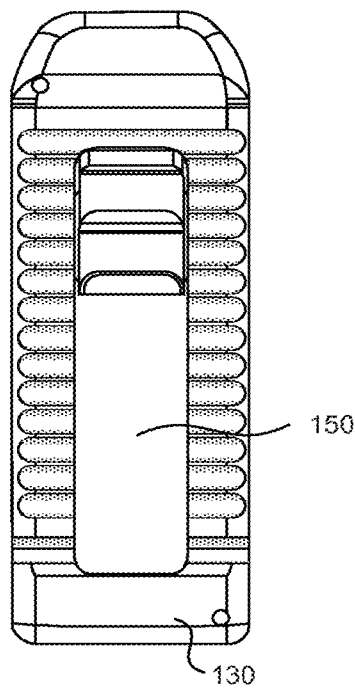
Figure 7A:
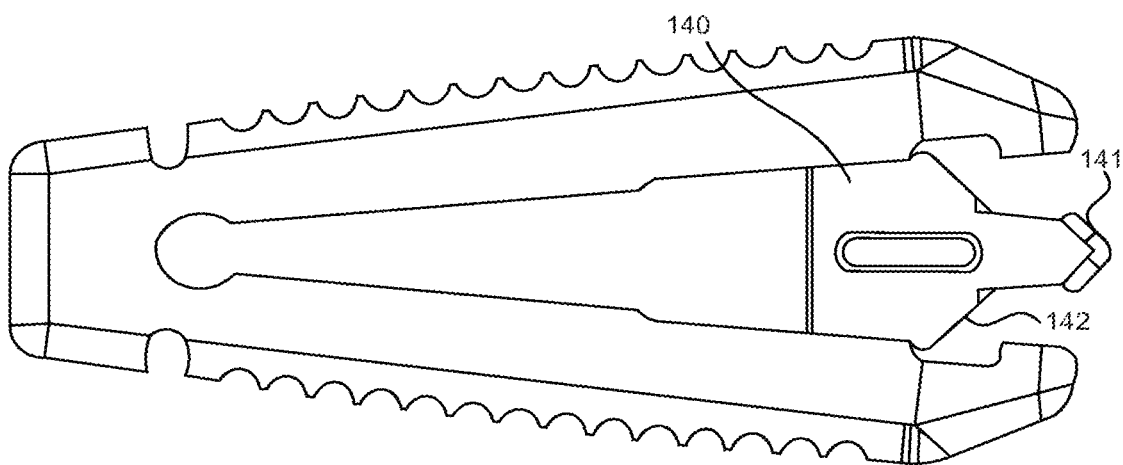
FIGS. 7A-7C are side views of an expandable fusion cage according to various embodiments described herein.
Figure 7B:
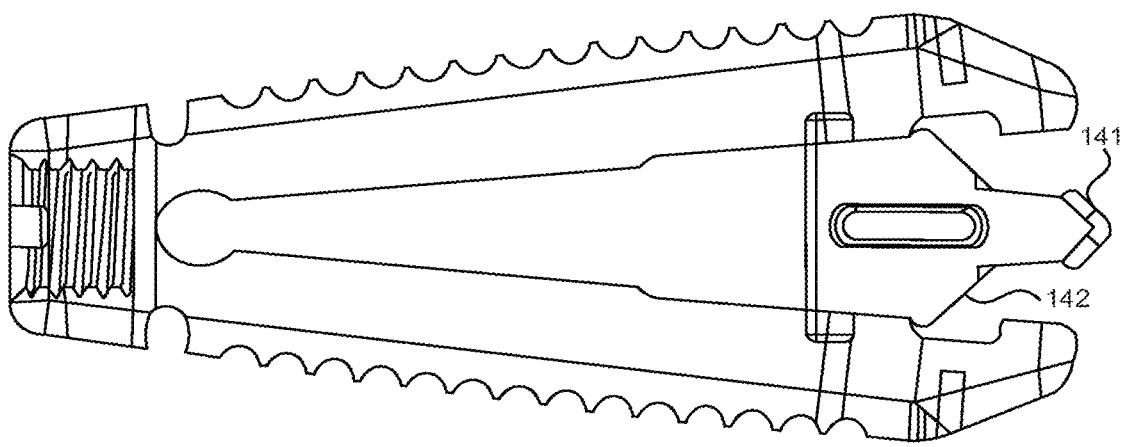
Figure 7C:
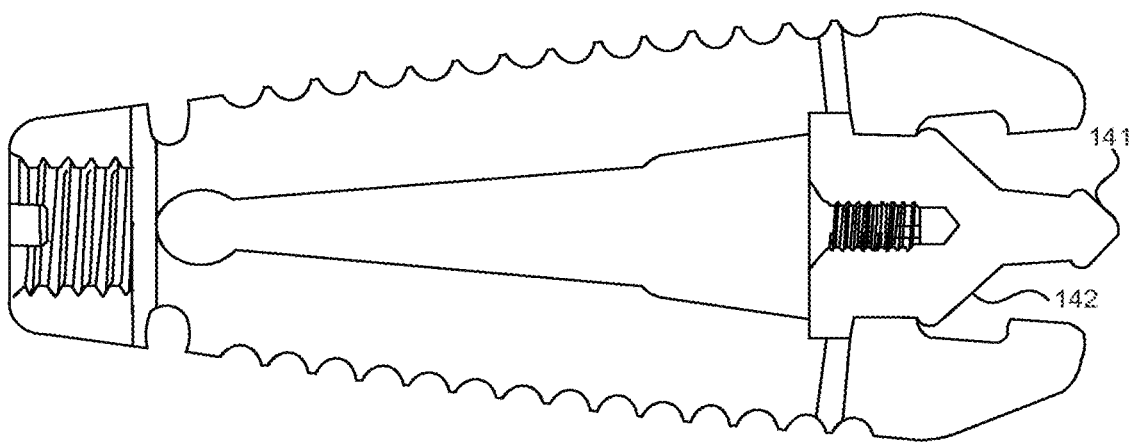
Figure 8B:
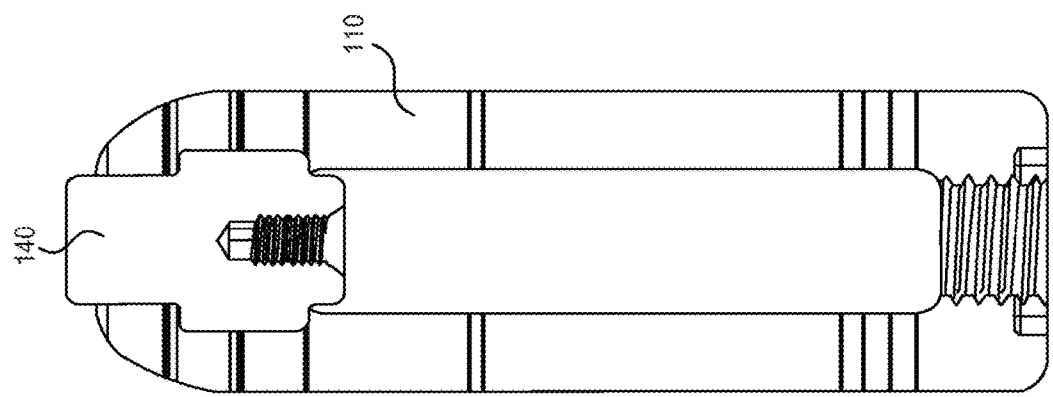
FIGS. 8A and 8B are a top and top see-through view of an expandable fusion cage according to various embodiments described herein.
Figure 8A:
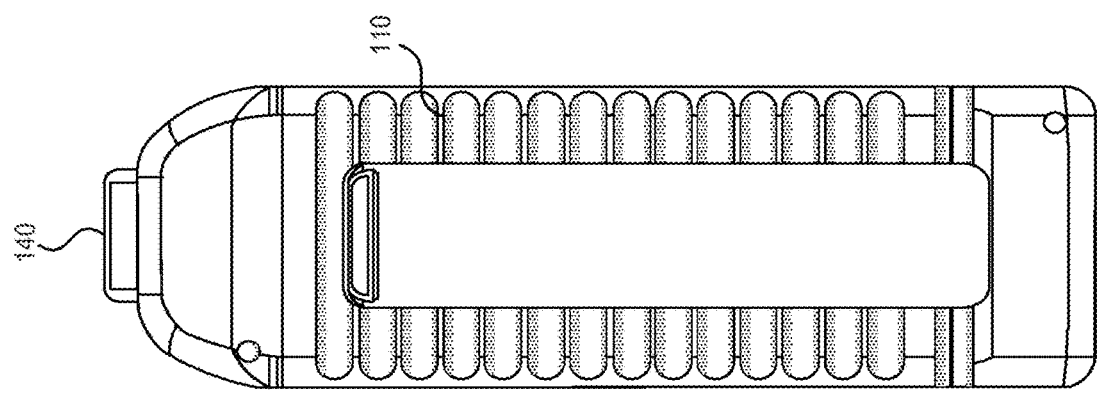
Figure 9A:
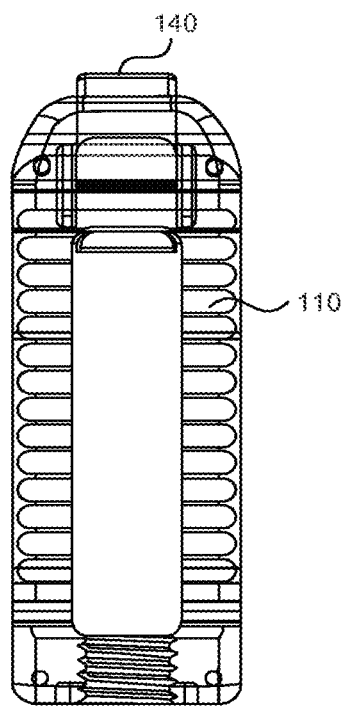
FIGS. 9A-9C are a top see-through, perspective, and perspective cross sectional view, respectively, of an expandable fusion cage according to various embodiments described herein.
Figure 9B:
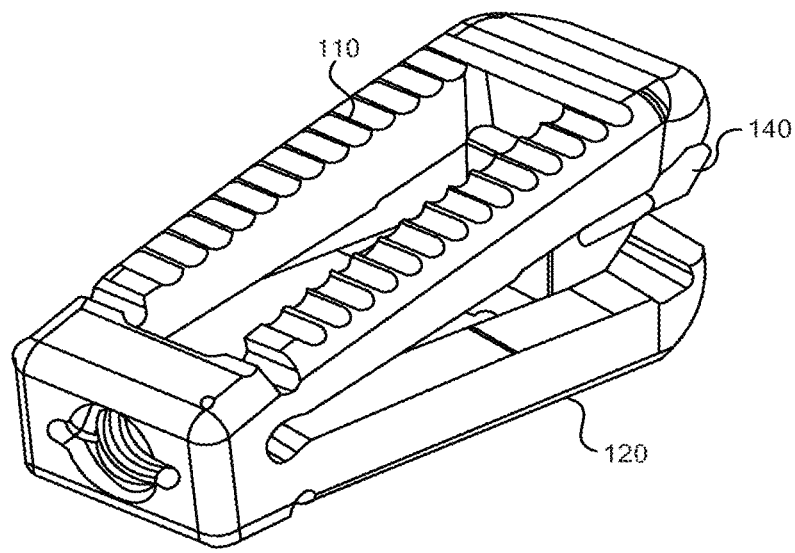
Figure 9C:
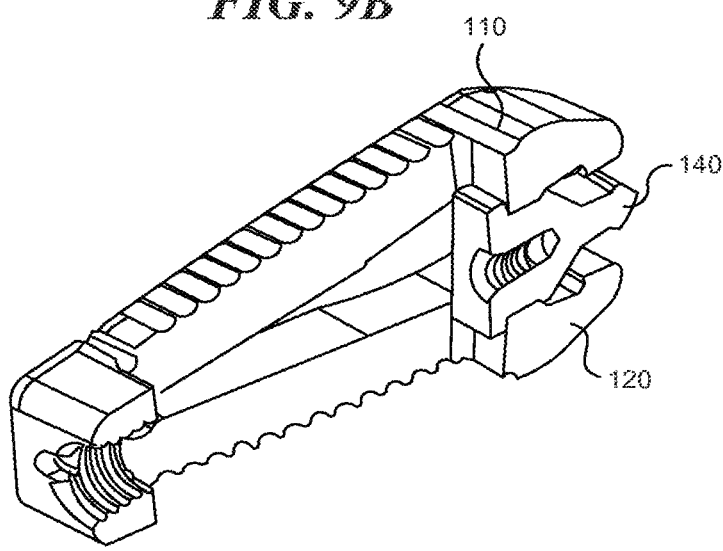
Figure 10A:
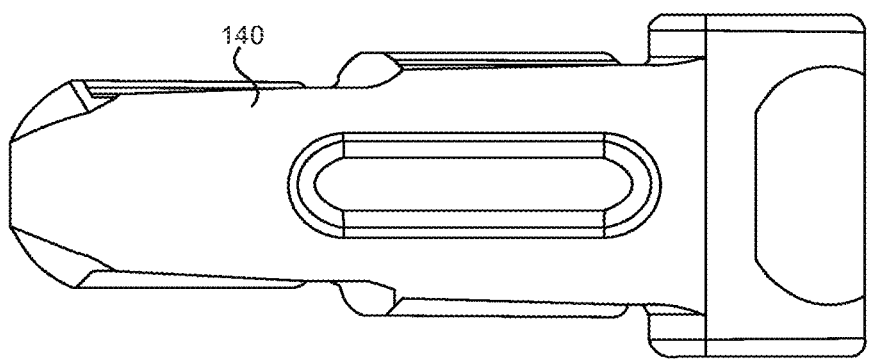
FIGS. 10A and 10B are perspective views of a slider for use in an expandable fusion cage according to various embodiments described herein.
Figure 10B:
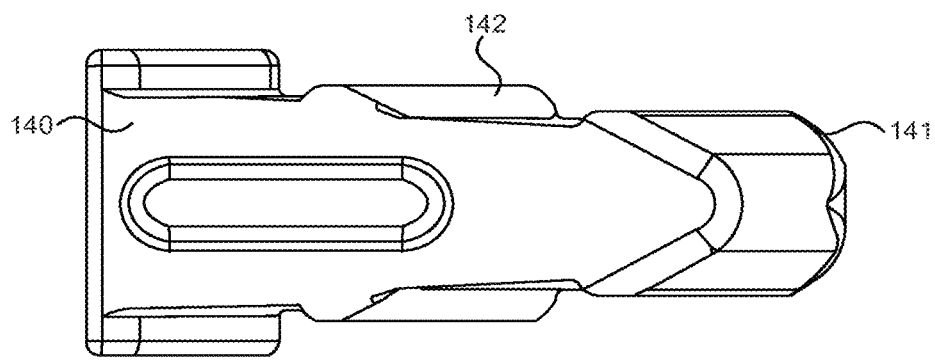
Figure 11A:
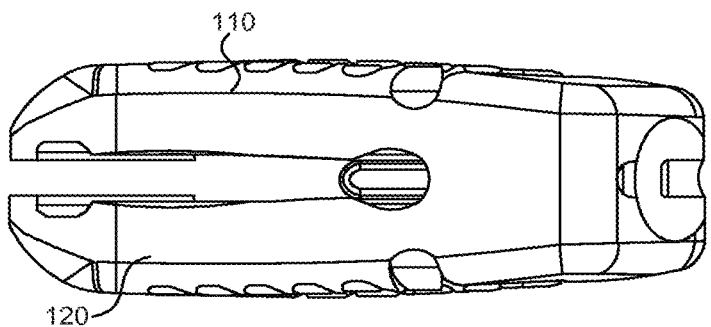
FIGS. 11A and 11B are perspective views of an expandable fusion cage according to various embodiments described herein.
Figure 11B:
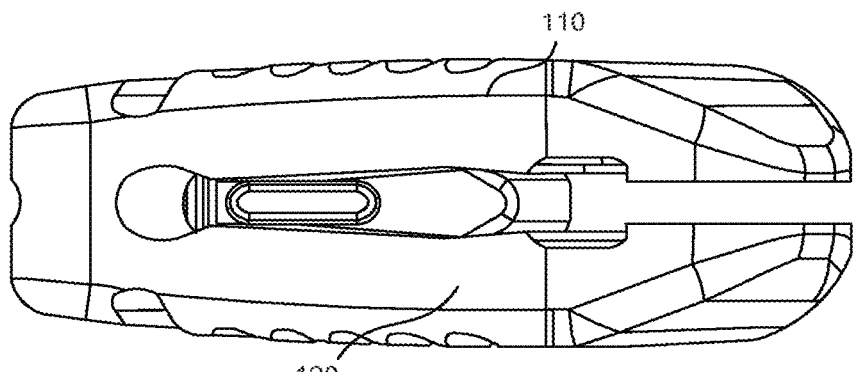
Figure 12A:
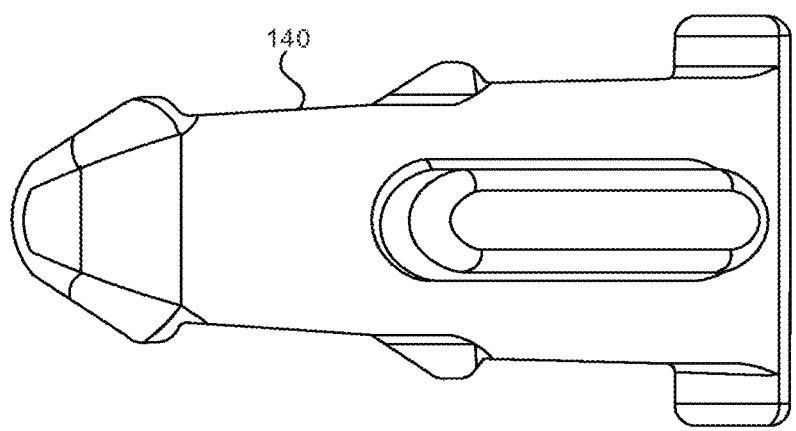
FIGS. 12A and 12B are perspective views of a slider for use in an expandable fusion cage according to various embodiments described herein.
Figure 12B:
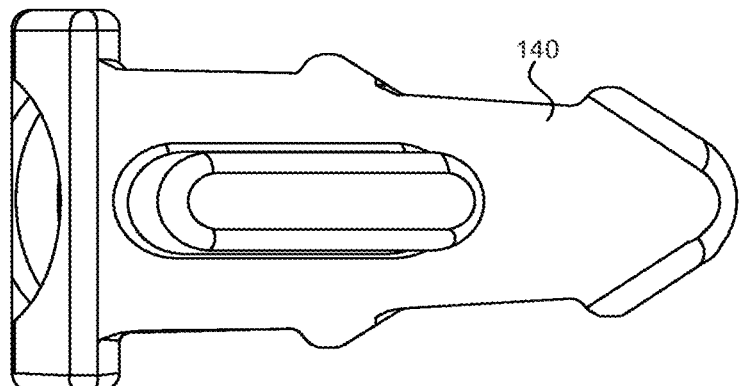
Figure 13:
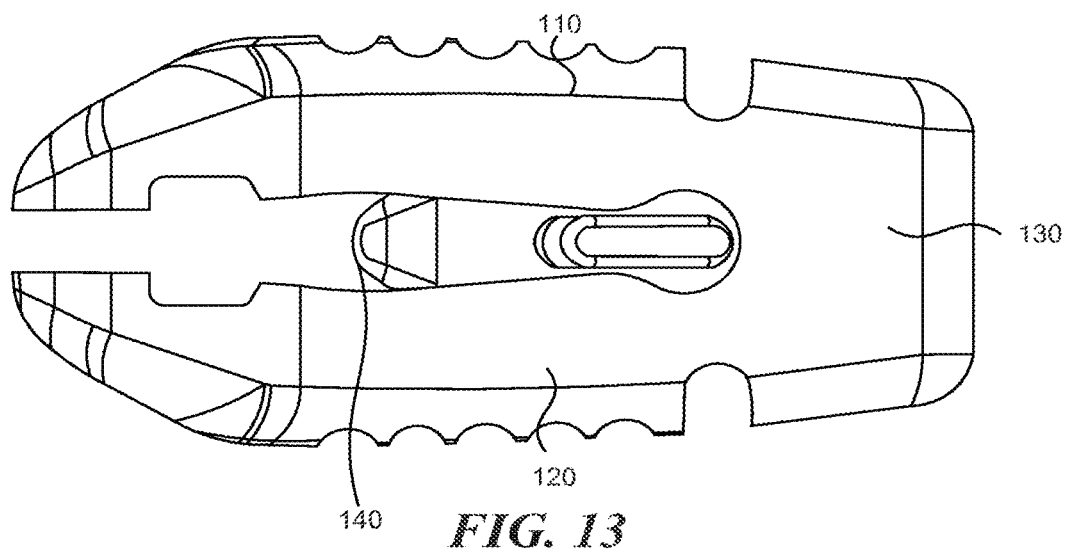
FIG. 13 is a side view of an expandable fusion cage according to various embodiments described herein.
Figure 14:
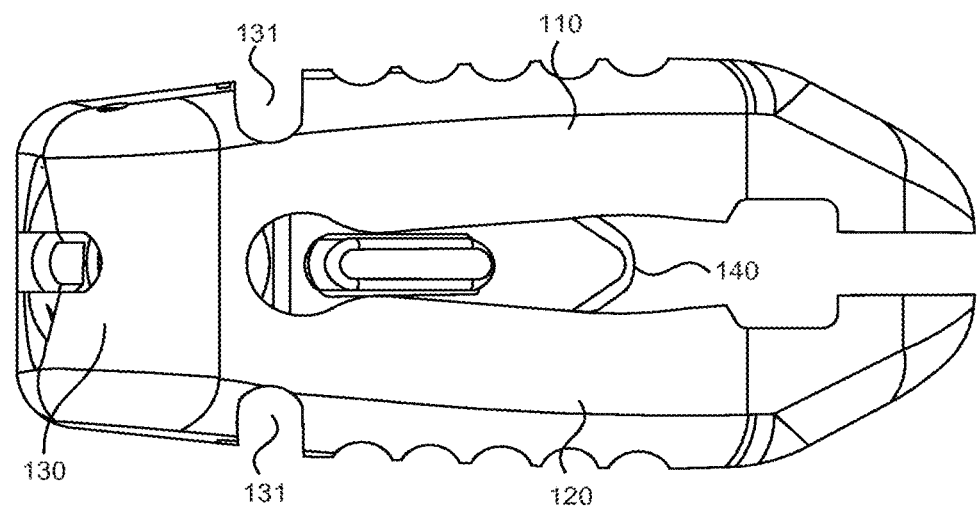
FIG. 14 is a side view of an expandable fusion cage according to various embodiments described herein.
Figure 15A:
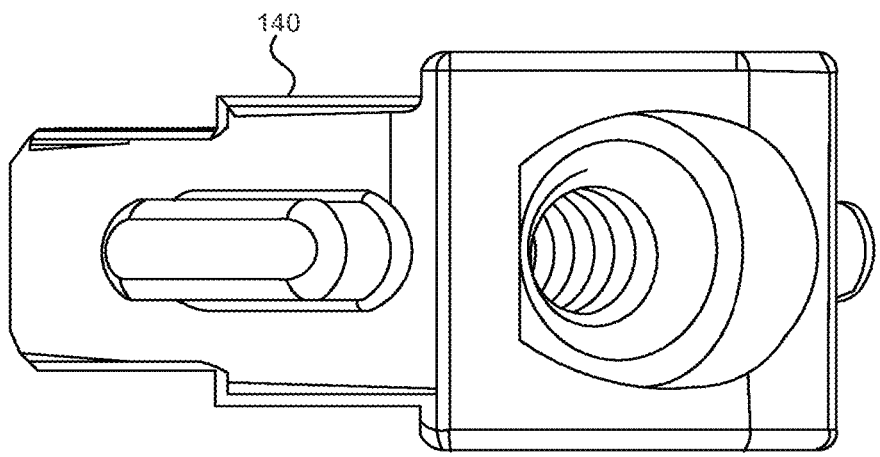
FIGS. 15A and 15B are perspective views of a slider for use in an expandable fusion cage according to various embodiments described herein.
Figure 15B:
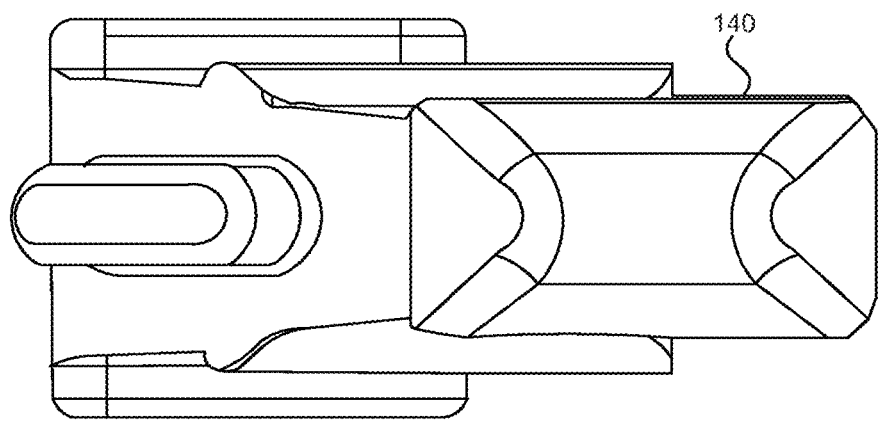
Figure 16A:
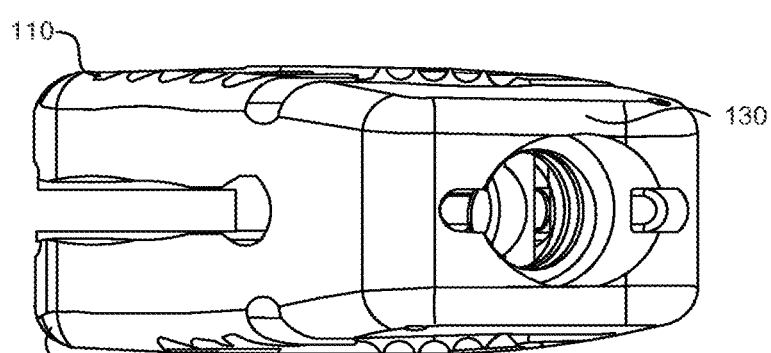
FIGS. 16A and 16B are perspective views of an expandable fusion cage according to various embodiments described herein.
Figure 16B:
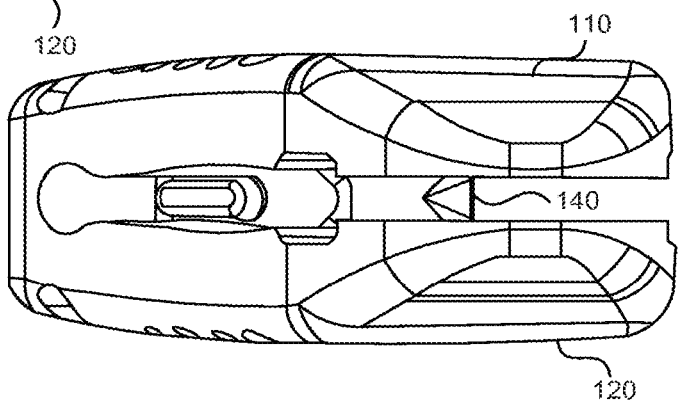
Figure 17A:
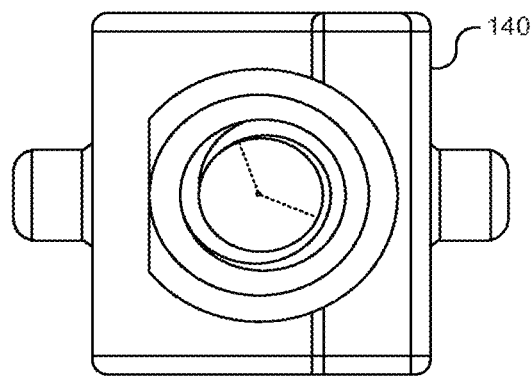
FIGS. 17A and 17B are front and back end views of a slider for use in an expandable fusion cage according to various embodiments described herein.
Figure 17B:
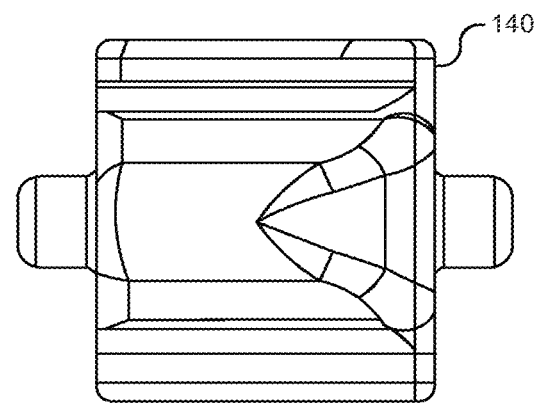
Figure 18A:
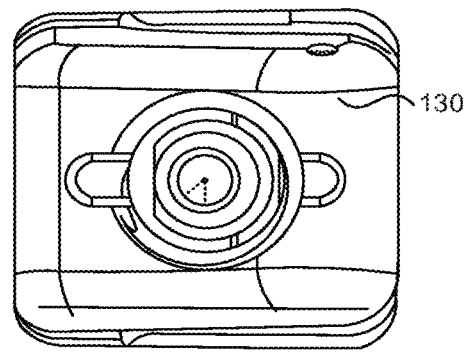
FIGS. 18A and 18B are front and back end views of an expandable fusion cage according to various embodiments described herein.
Figure 18B:
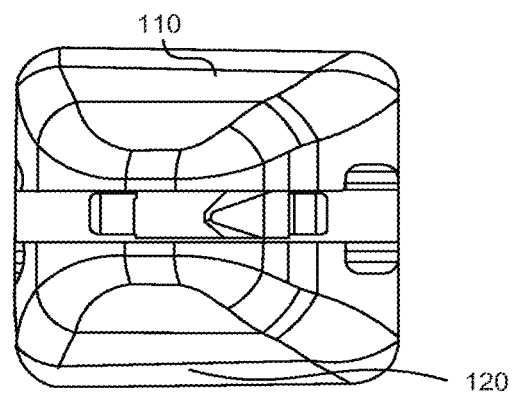
Figure 19A:
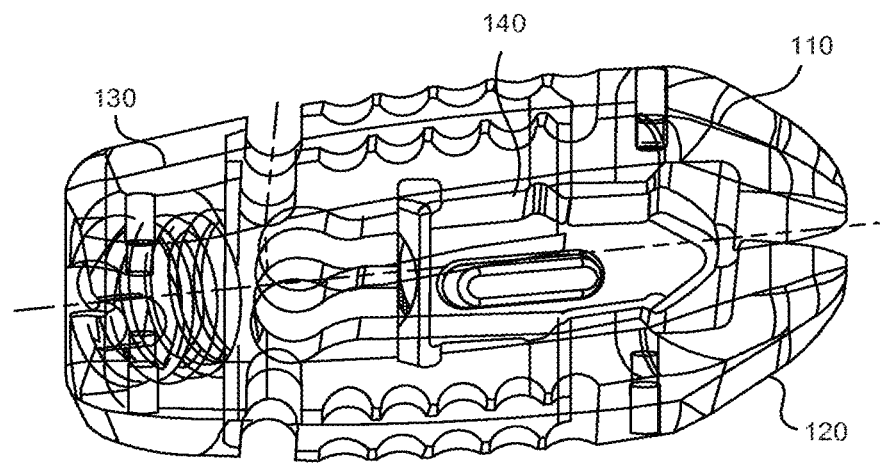
FIGS. 19A-19C are a perspective see-through, a perspective see-through, and a perspective view, respectively, of an expandable fusion cage according to various embodiments described herein.
Figure 19B:
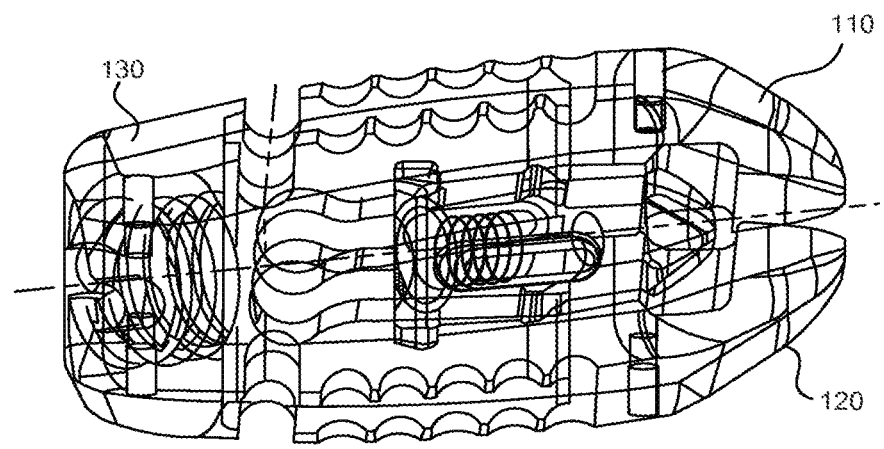
Figure 19C:
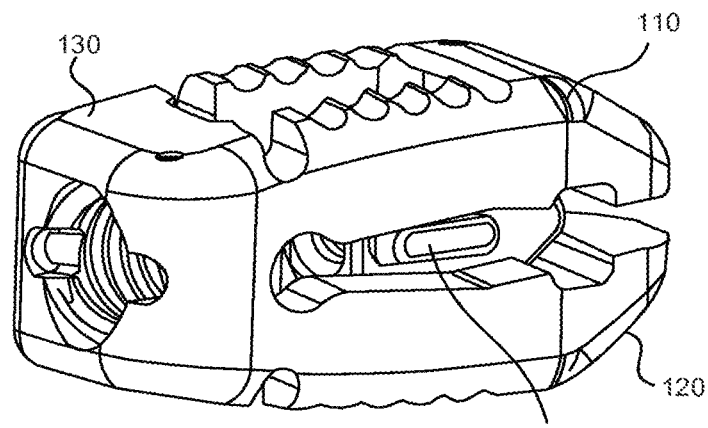
Figure 20:
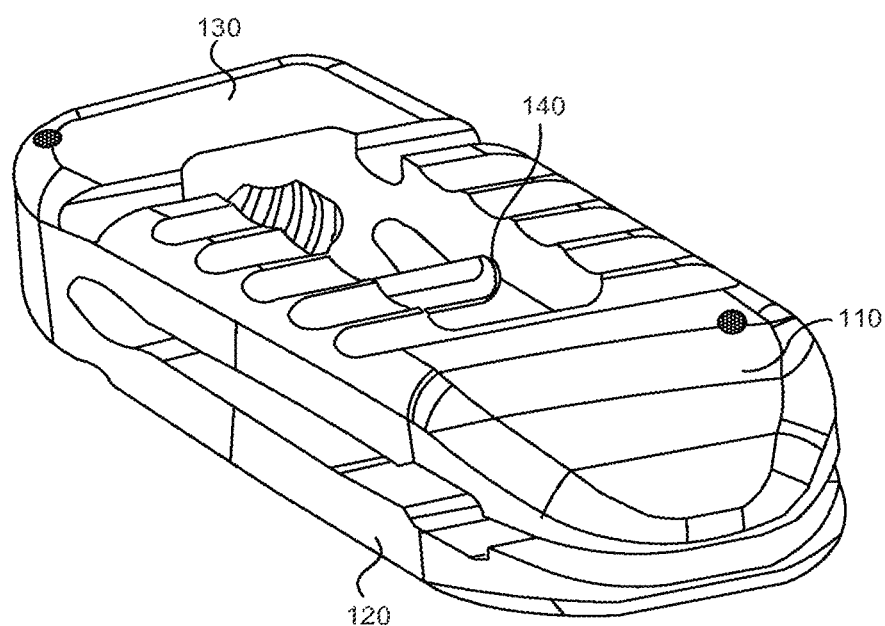
FIG. 20 is a perspective view of an expandable fusion cage according to various embodiments described herein.
Figure 21B:
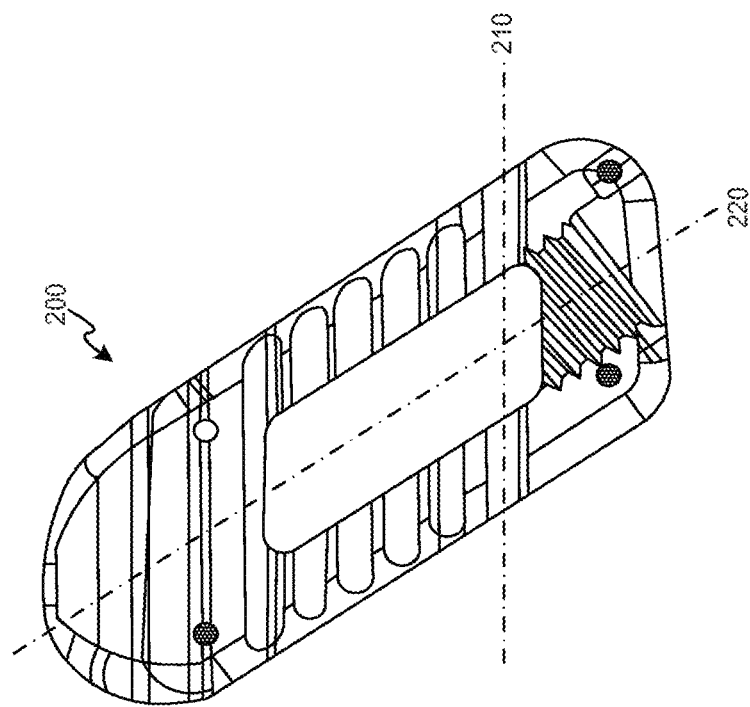
Figure 21A:
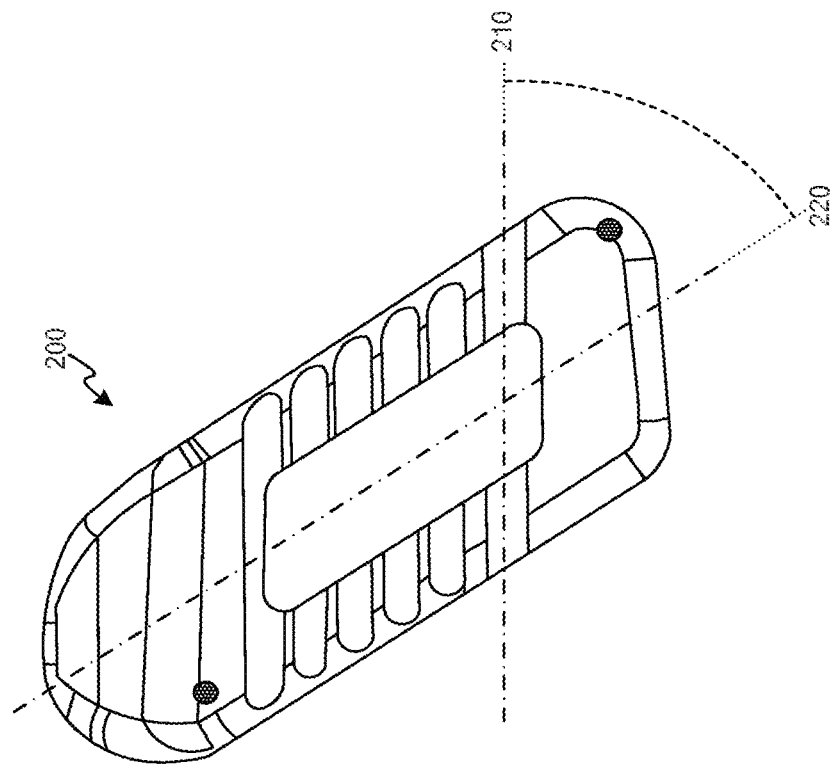
Figure 22A:
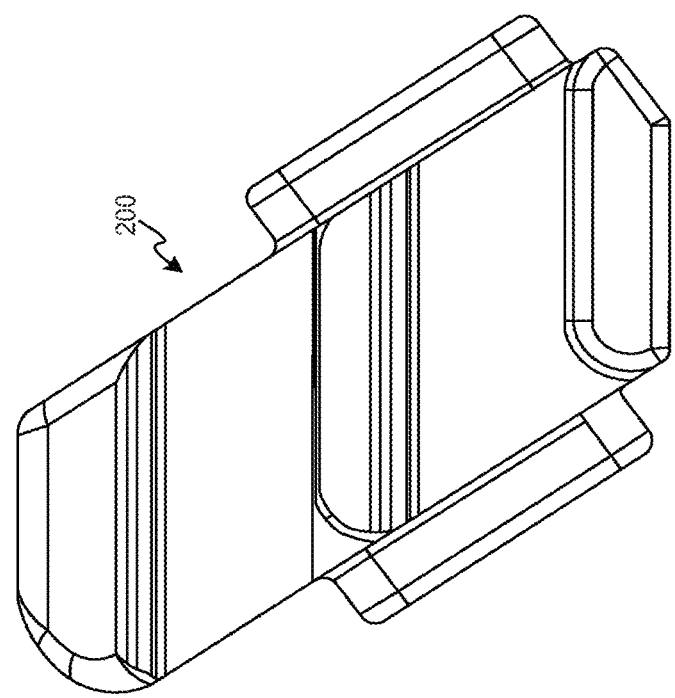
Figure 22B:
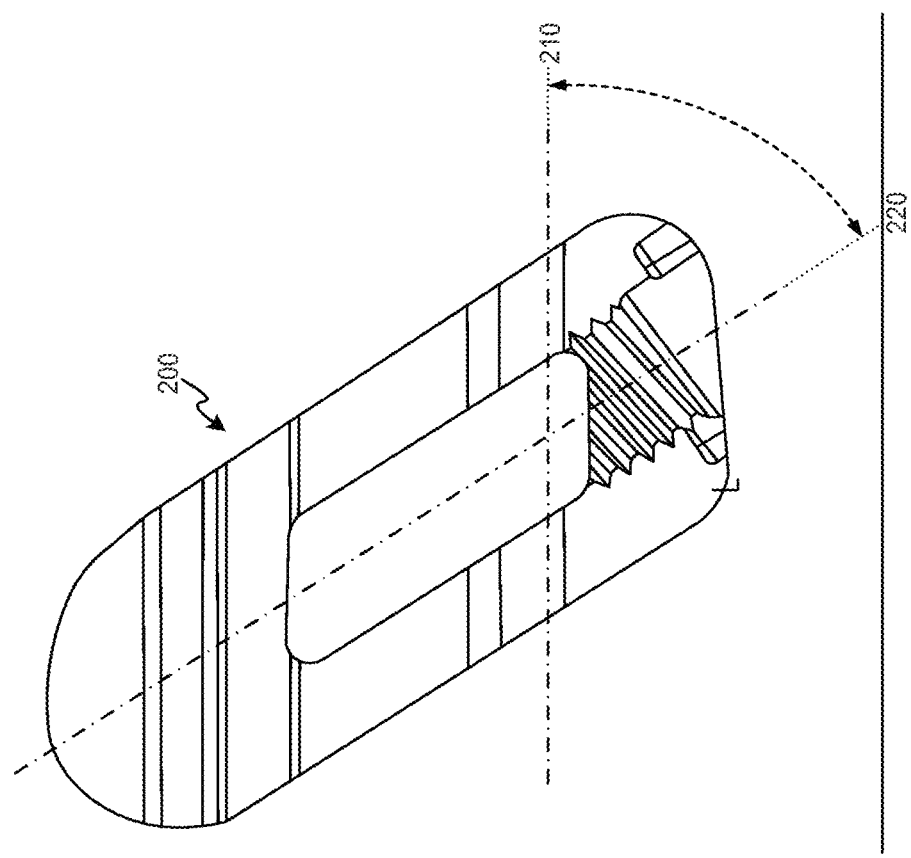
Figure 23B:
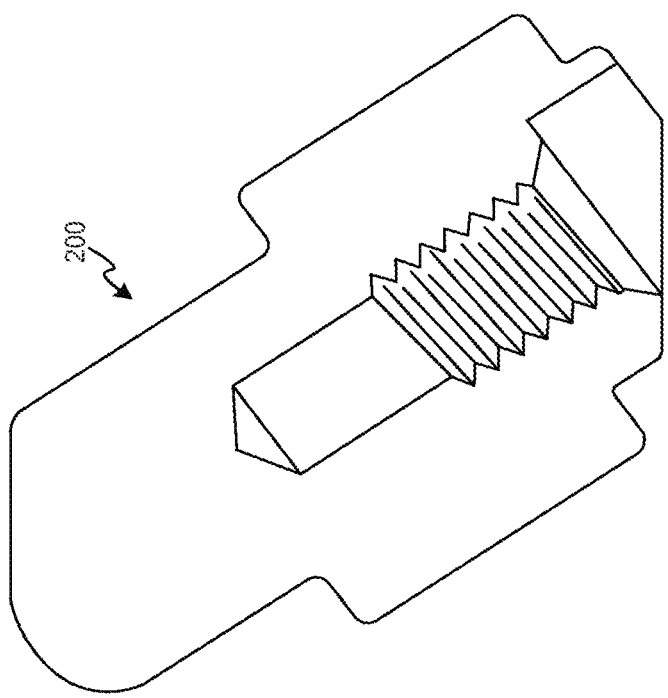
Figure 23A:
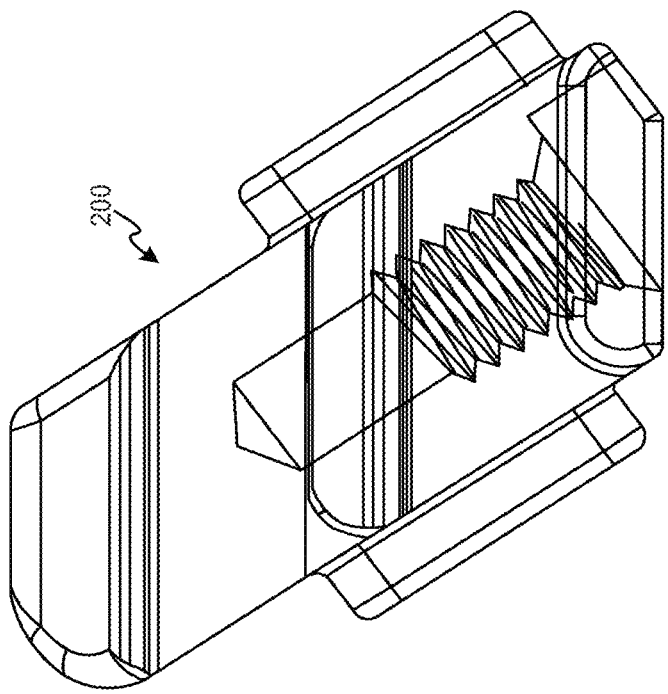
Figure 24B:
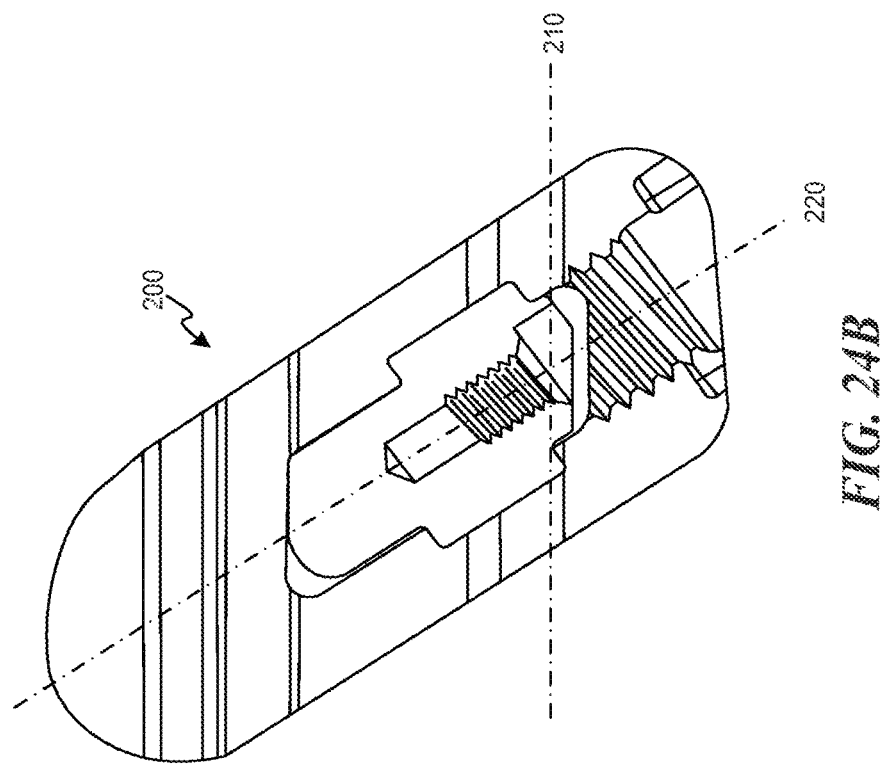
Figure 24A:
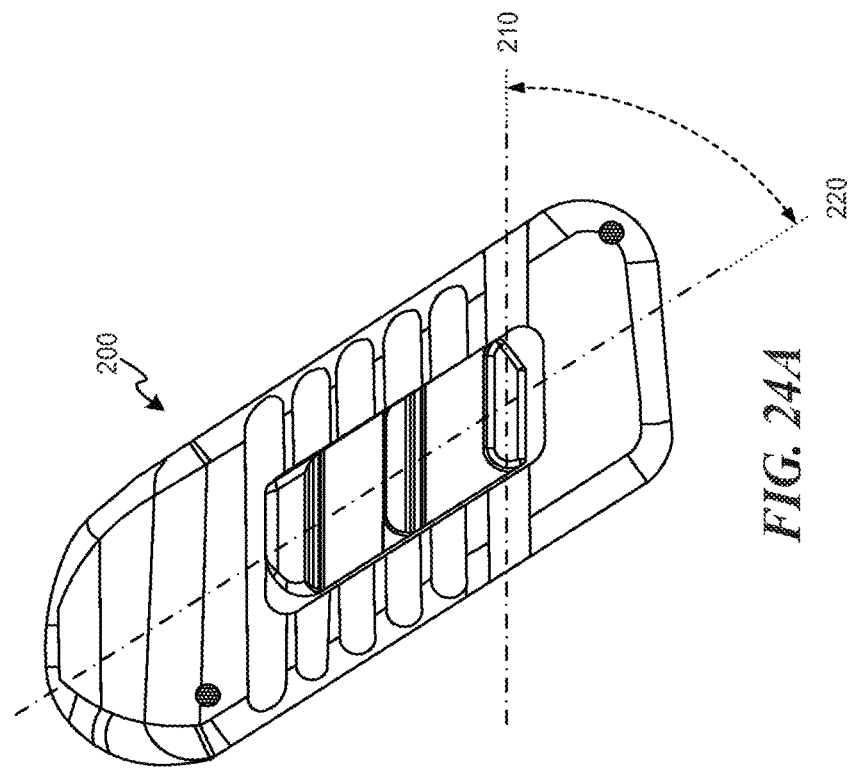
Figure 25B:
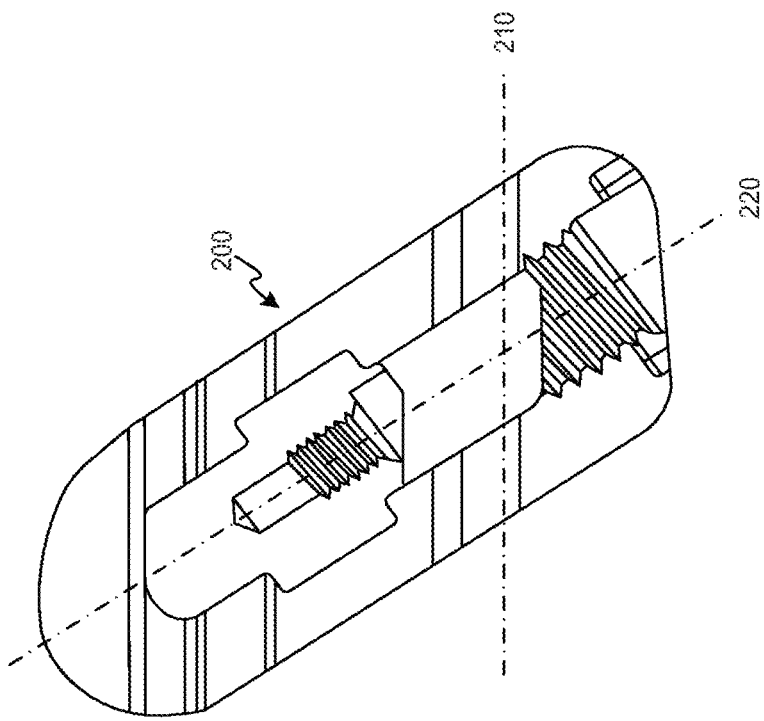
Figure 25A:
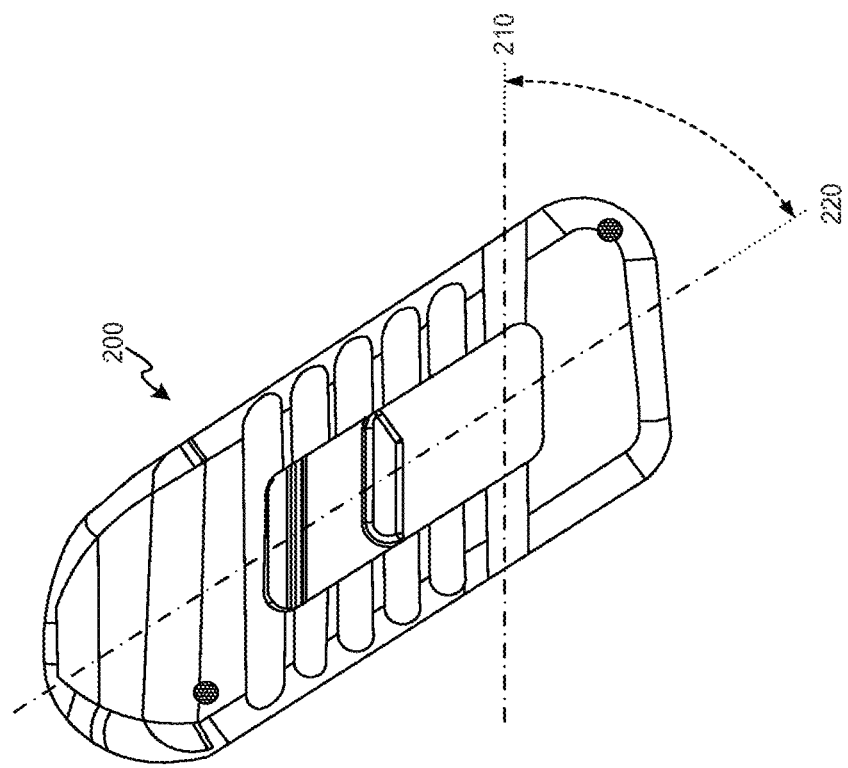
Figure 26B:
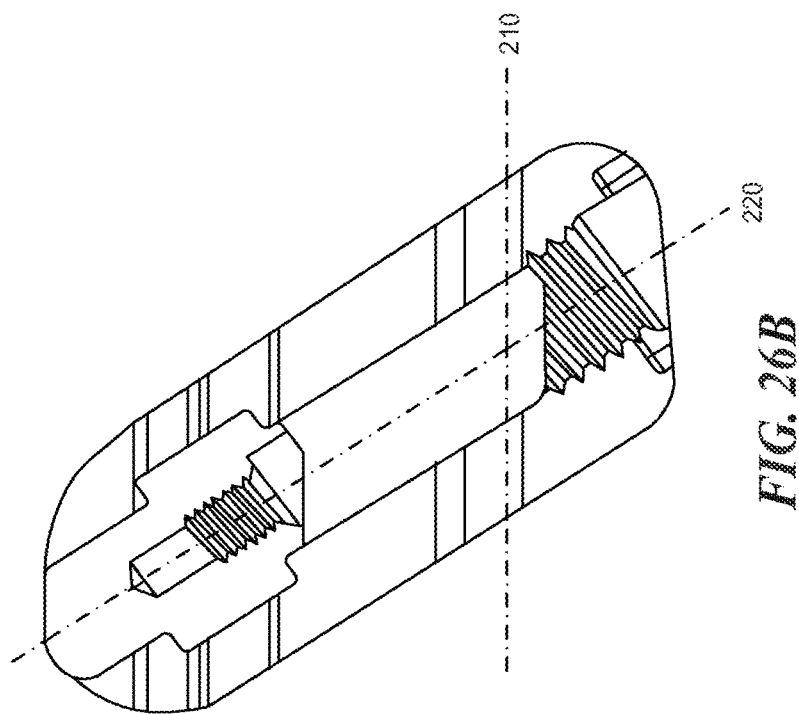
Figure 26A:
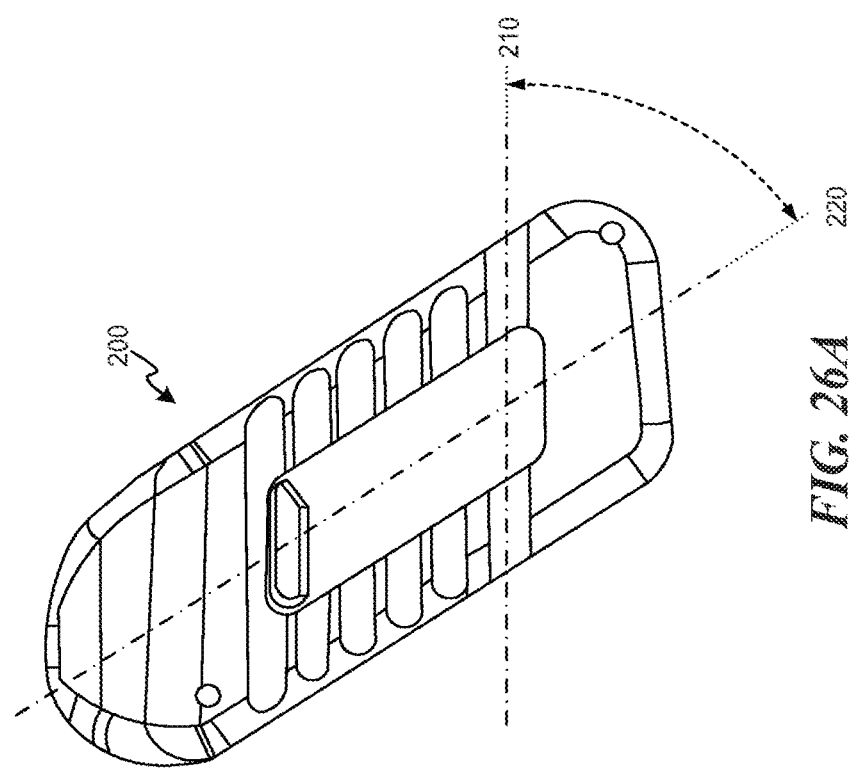
Figure 28:
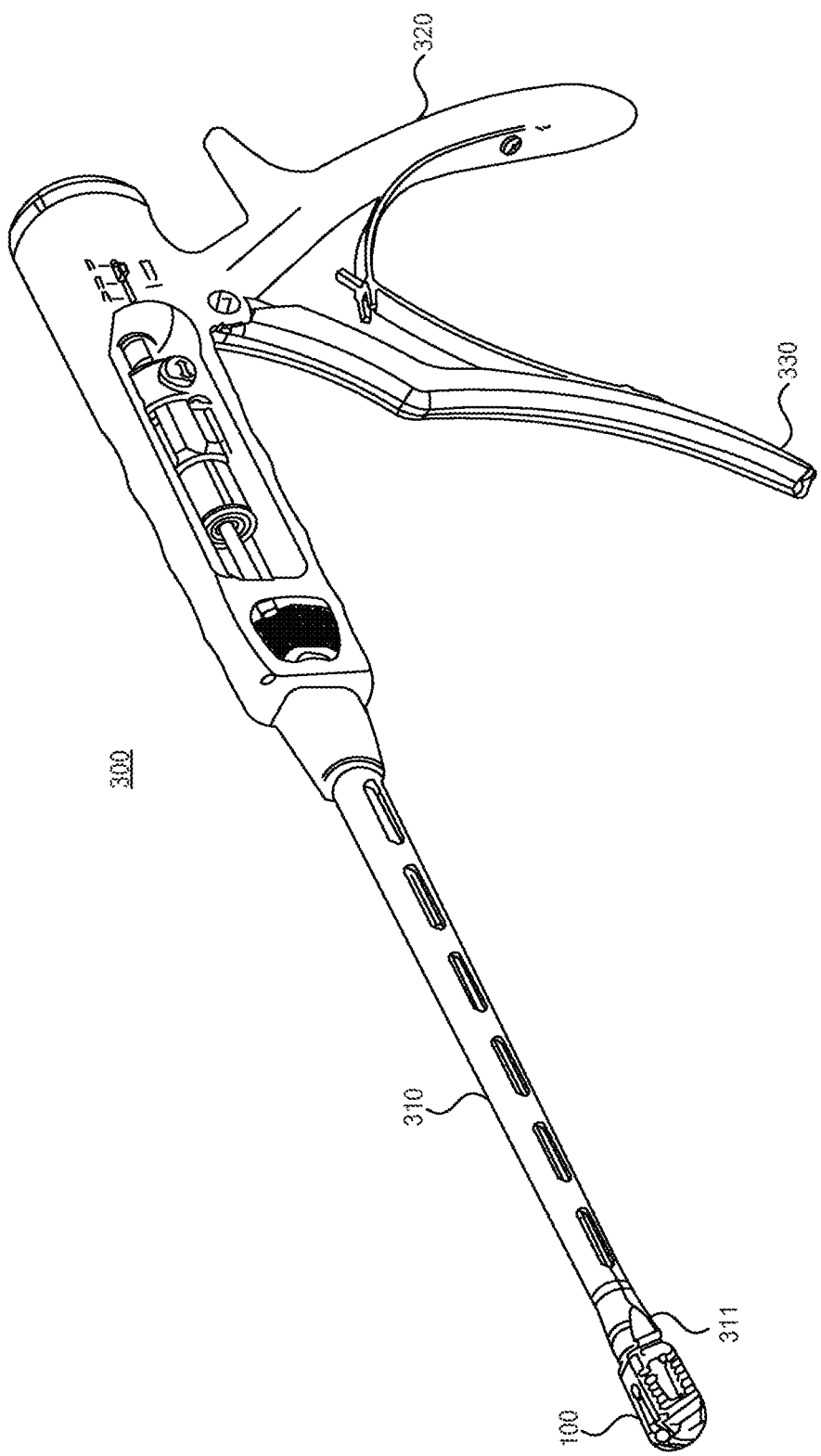
FIG. 28 is a perspective view of an implant inserter according to various embodiments described herein.
Figure 29:
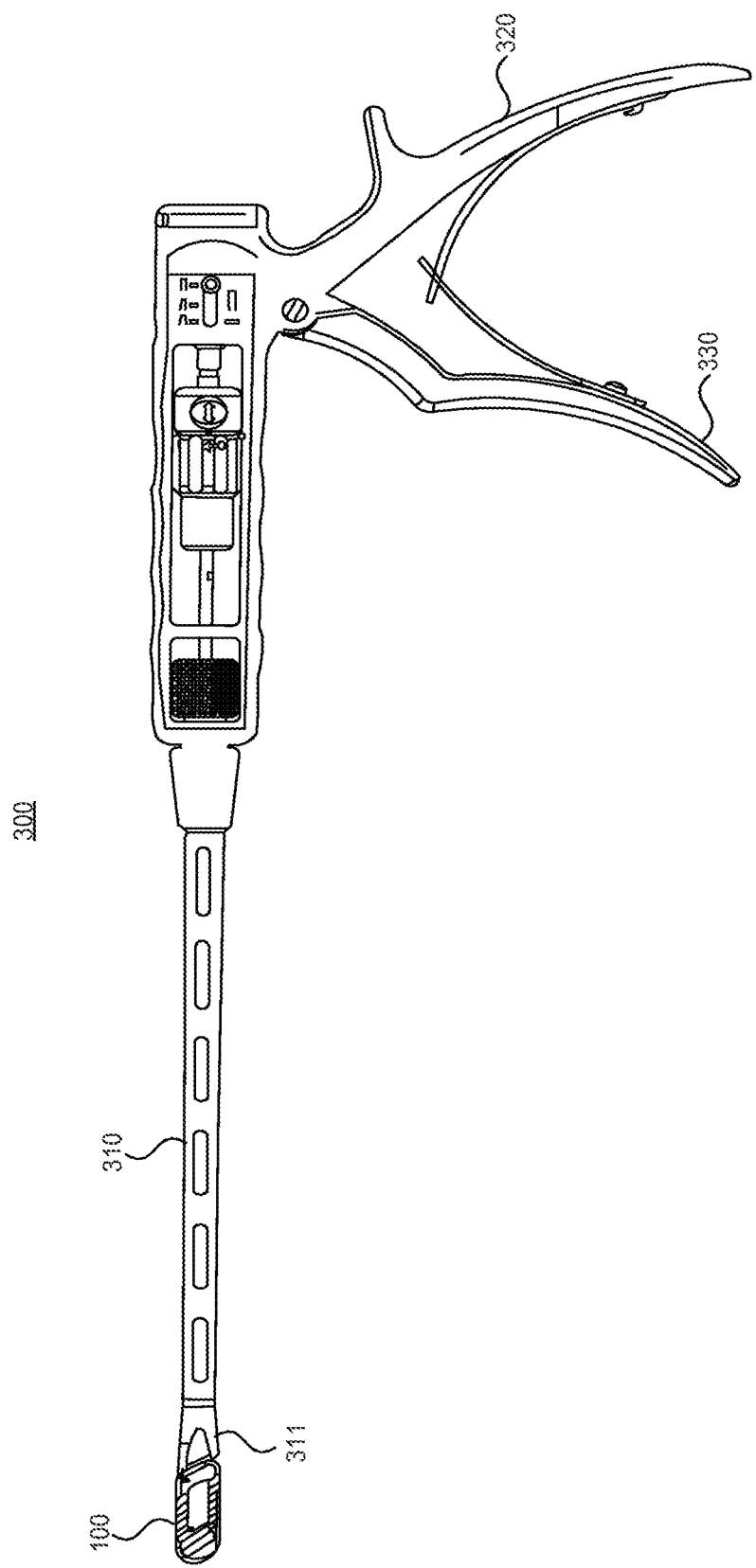
FIG. 29 is a side view of the implant inserter shown in FIG. 28.
Figure 30:
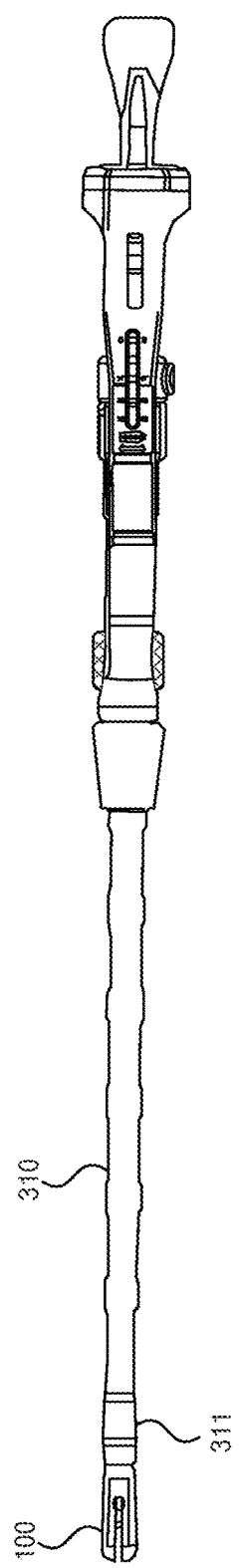
FIG. 30 is a top view of the implant inserter shown in FIG. 28.
Figure 31:
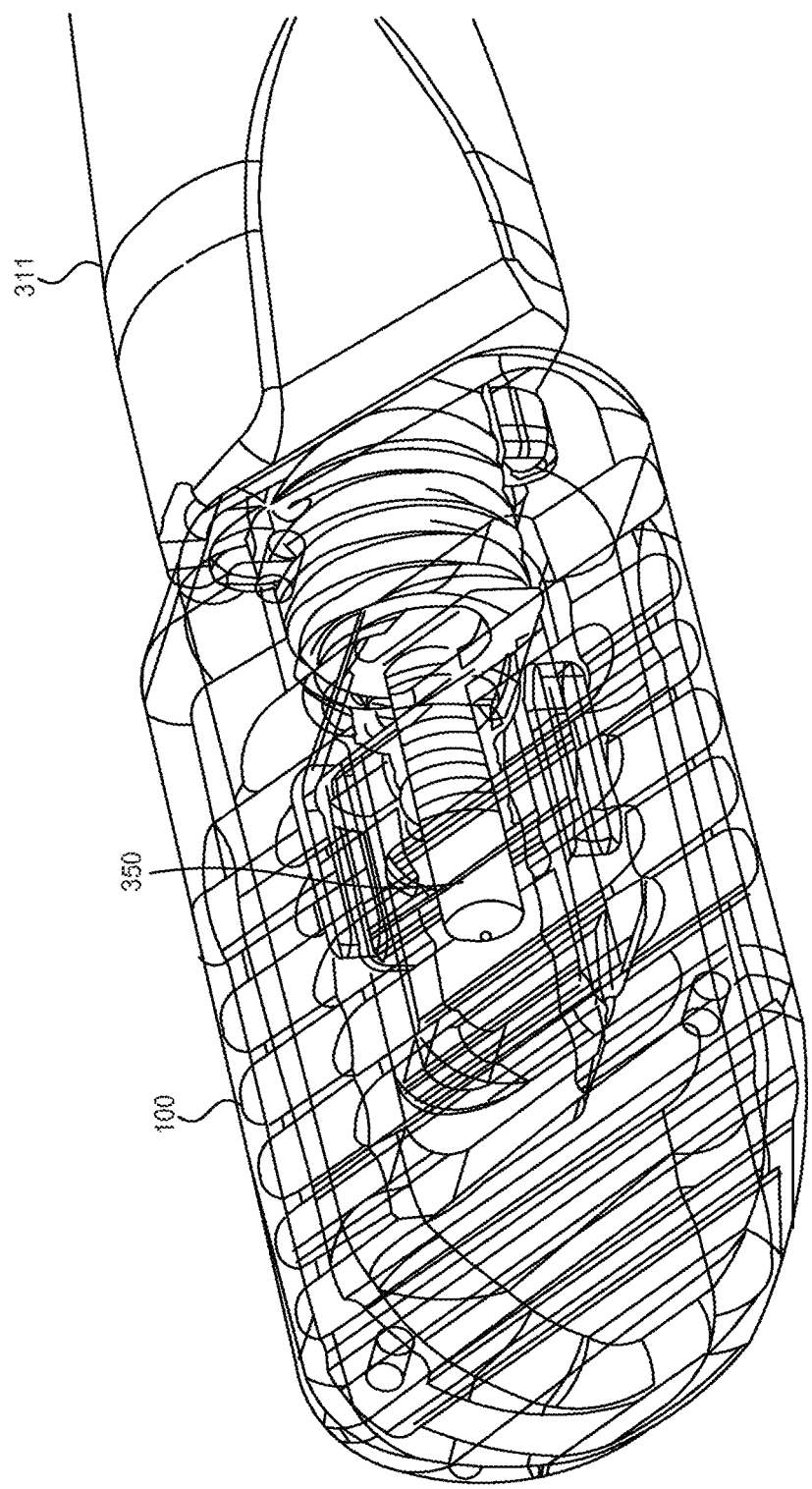
FIG. 31 is a see-through perspective view of the distal tip of the implant inserter shown in FIG. 28.
Figure 32:
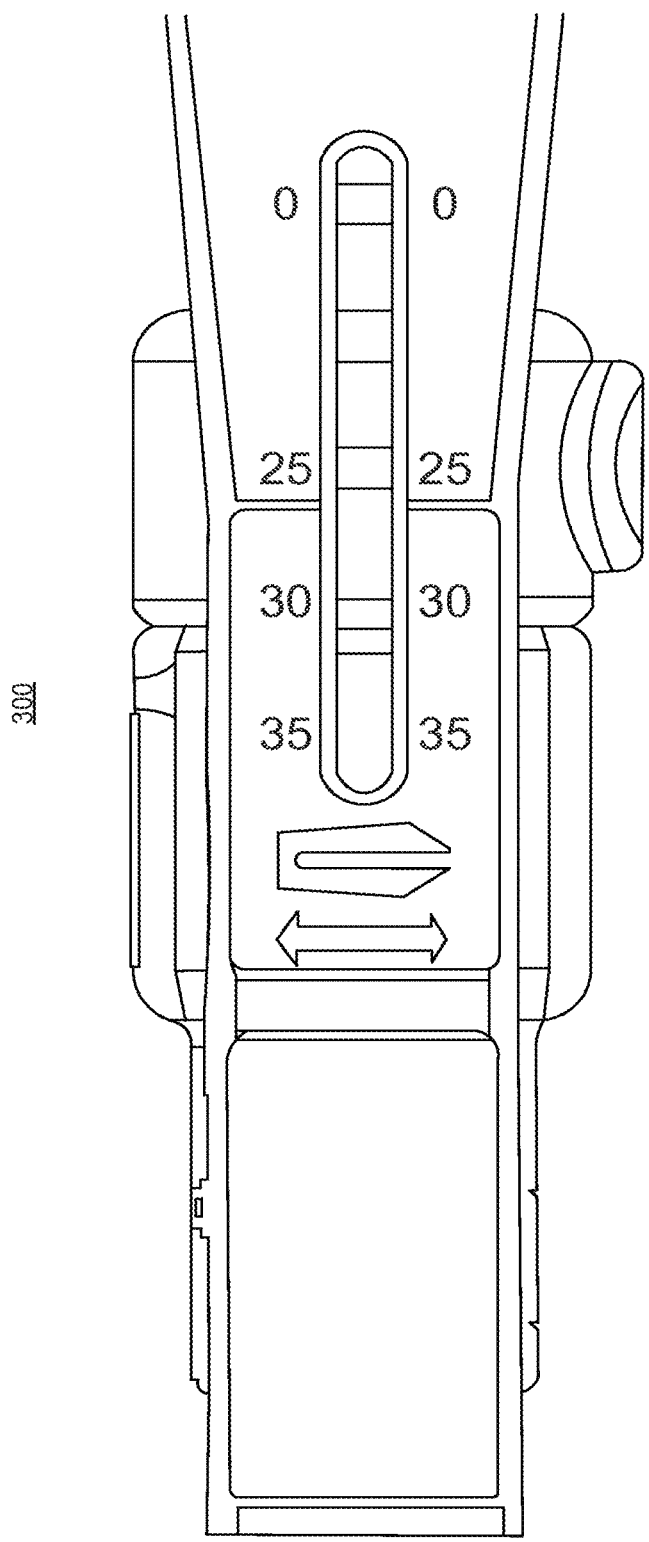
FIG. 32 is a close up top view of the implant inserter shown in FIG. 28.
Figure 33:
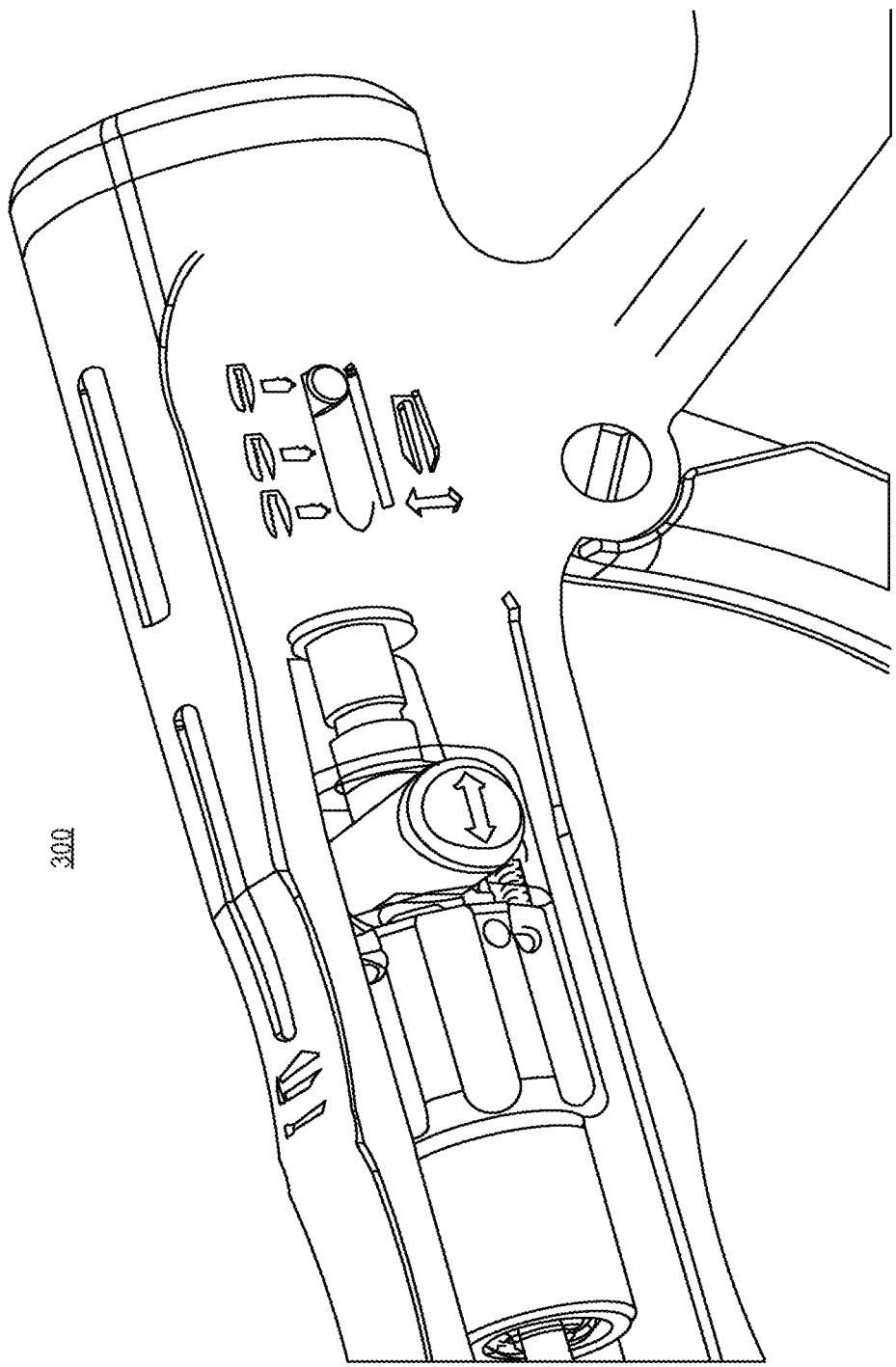
FIG. 33 is a close up perspective view of the a portion of the implant inserter shown in FIG. 28.
Figure 34:
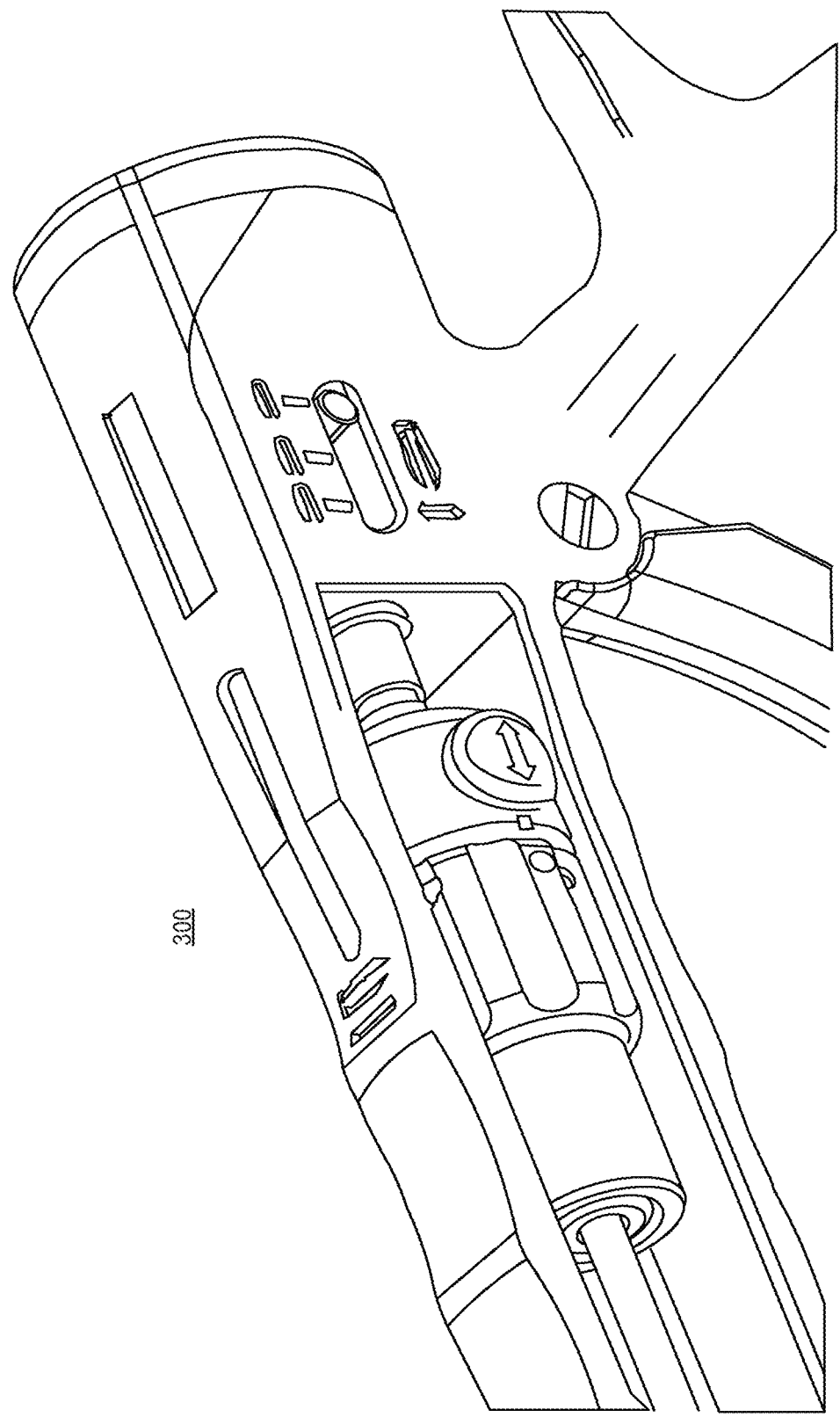
FIG. 34 is a close up perspective view of the a portion of the implant inserter shown in FIG. 28.
Figure 35:
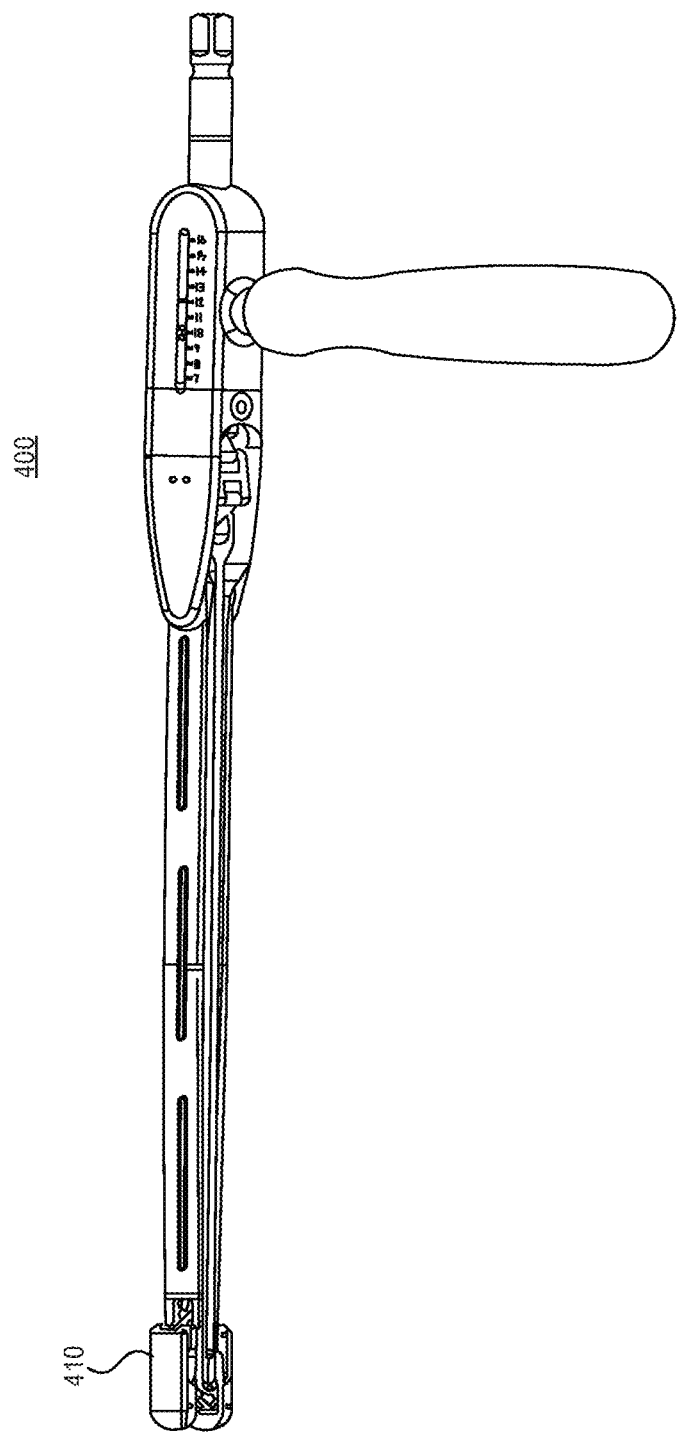
FIG. 35 is a perspective view of an expandable distractor instrument according to various embodiments described herein.
Figure 36:
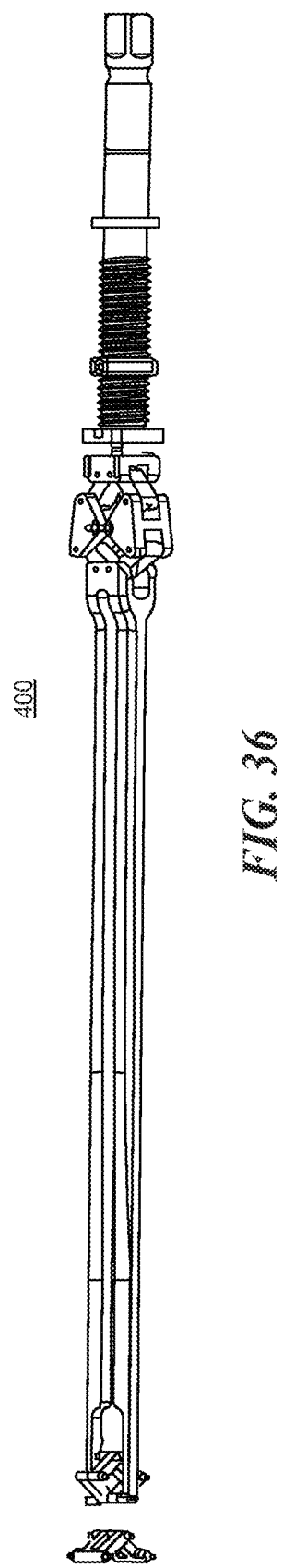
FIG. 36 is a perspective view of a mechanism included in the expandable distractor instrument shown in FIG. 35.
Figure 37:
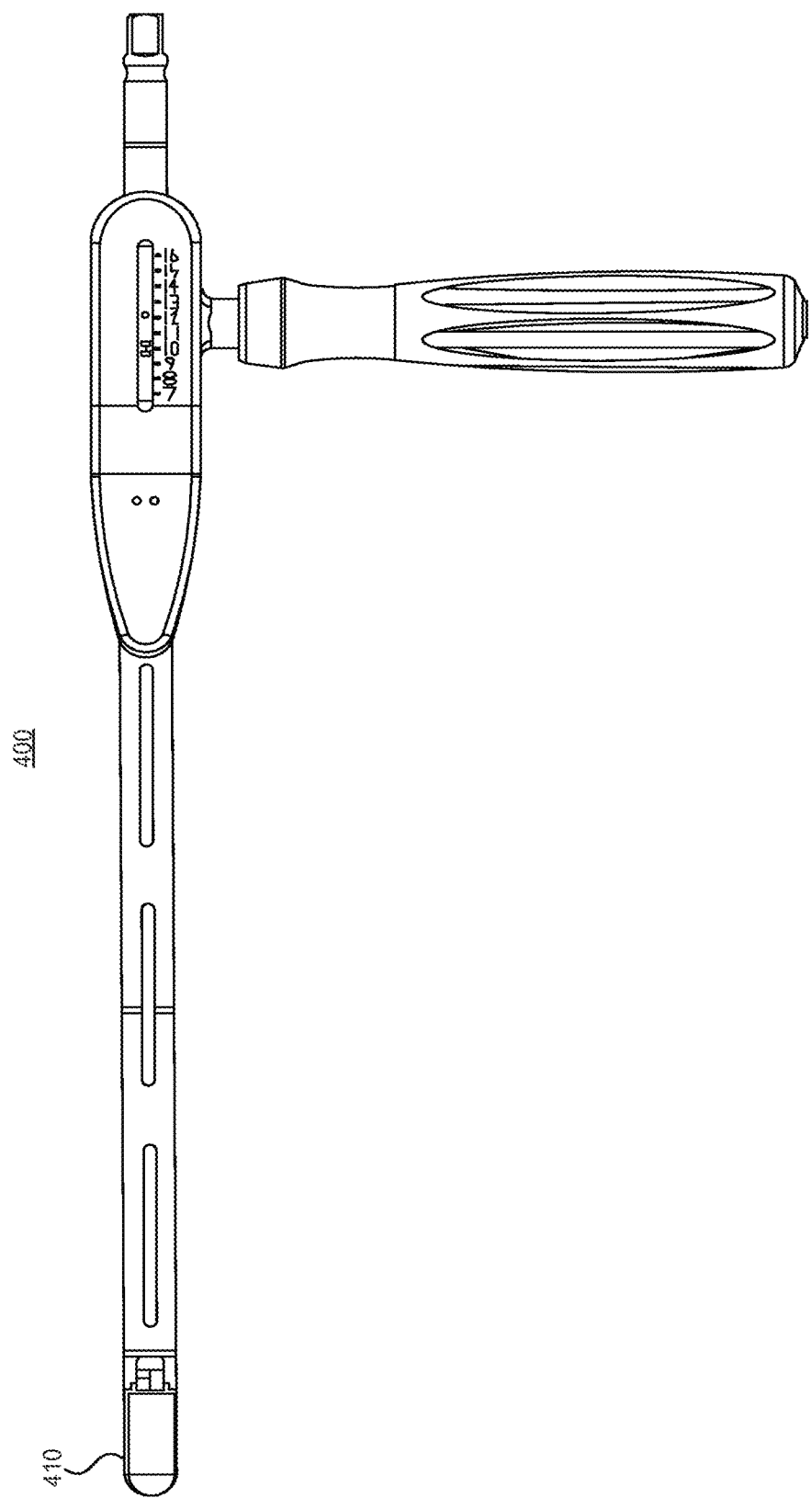
FIG. 37 is a side view of the expandable distractor instrument shown in FIG. 35.
Figure 38:
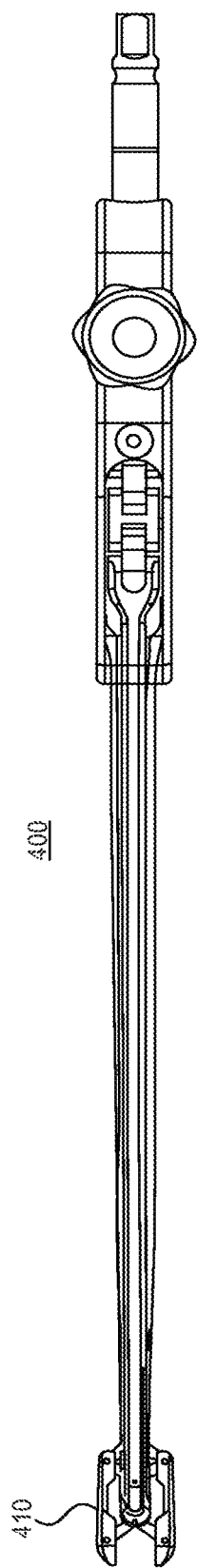
FIG. 38 is bottom view of the expandable distractor instrument shown in FIG. 35.
Figure 39:
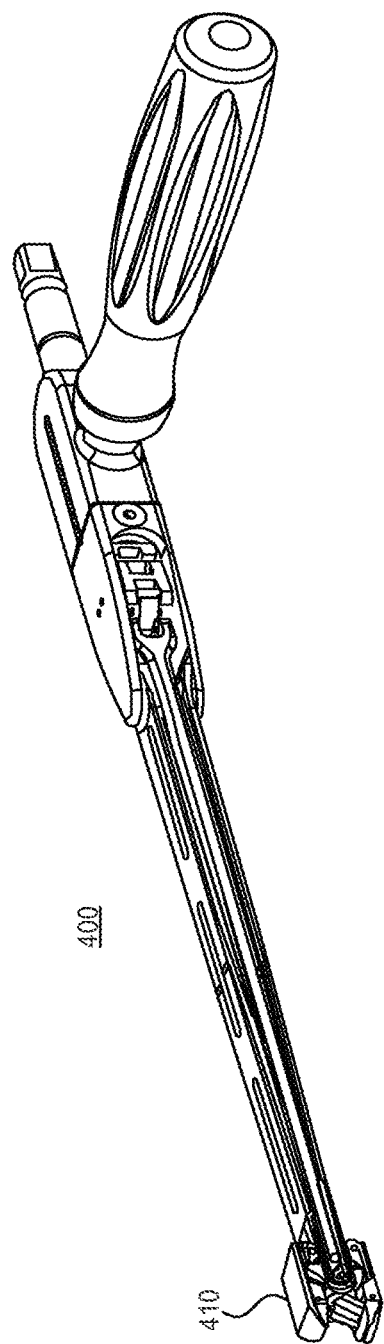
FIG. 39 is a bottom perspective view of the expandable distractor instrument shown in FIG. 35.
Figure 40:
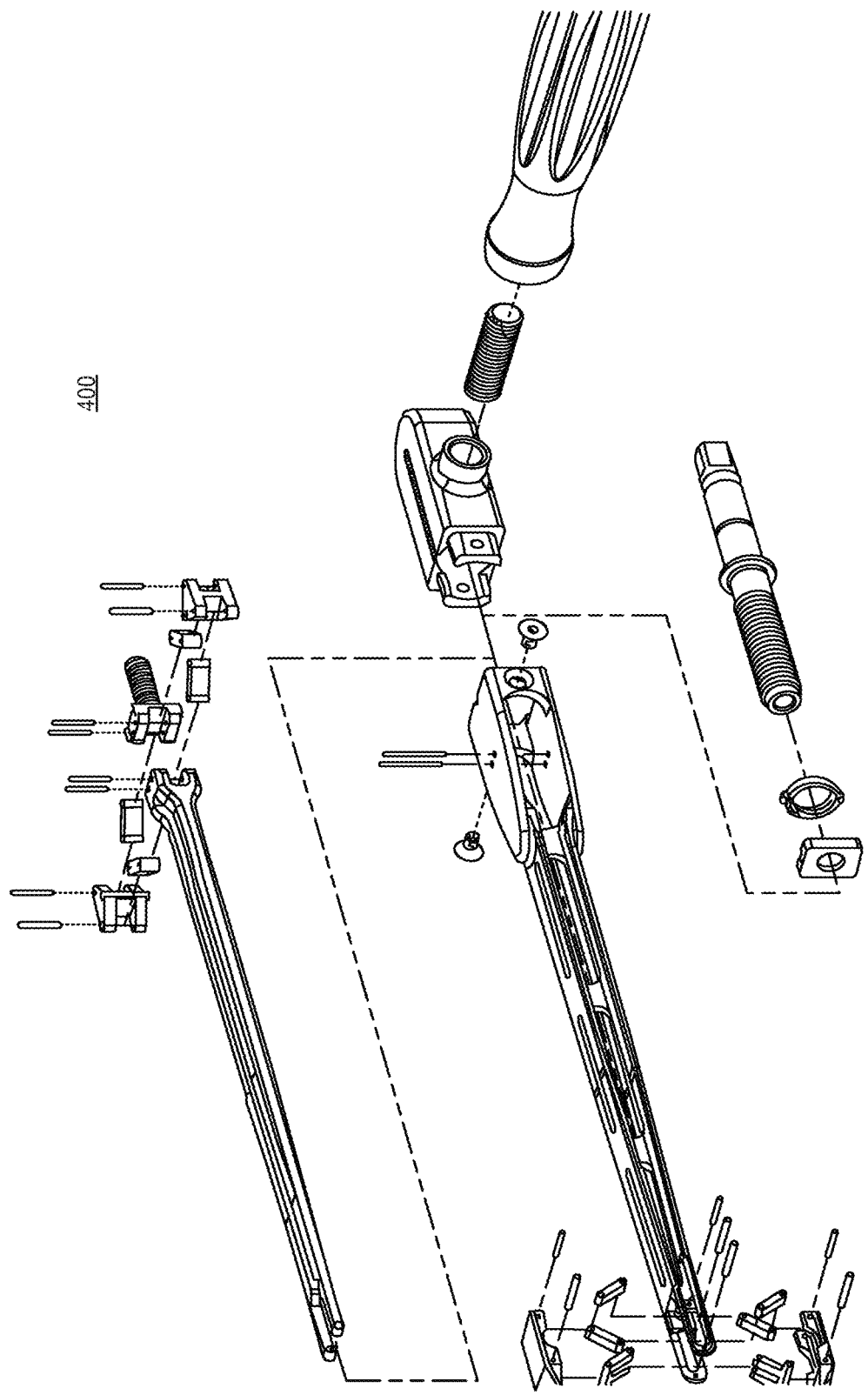
FIGS. 40 and 41 are exploded view of the expandable distractor instrument shown in FIG. 35.
Figure 41:
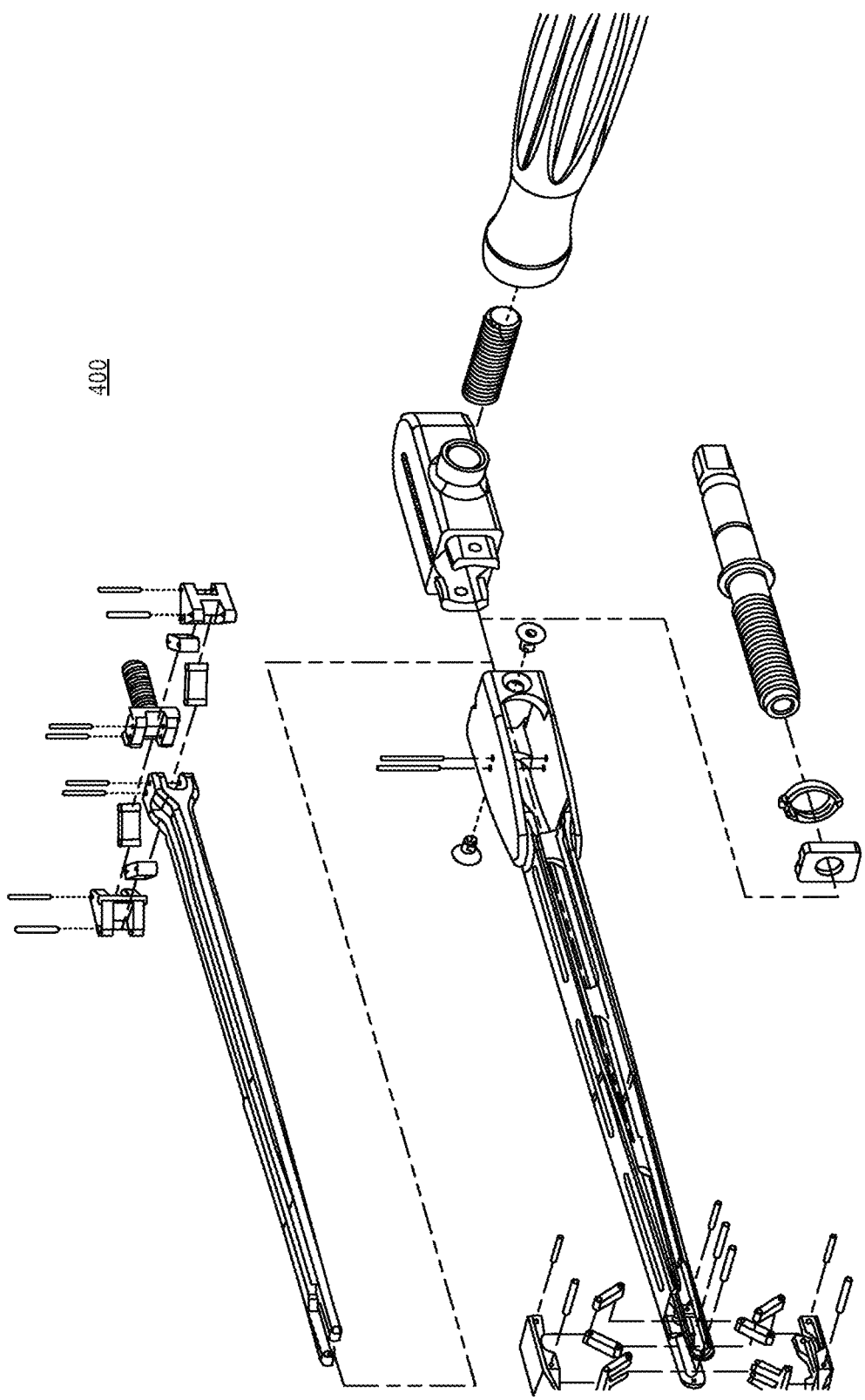

In some embodiments, one or more slots can be defined by the lower surfaces of the upper portion 110 and lower portion 120. With reference to FIG. 3A, the spinal implant can include a first slot 161 and a second slot 162. The spinal implant 100 can includes more or fewer slots. The slots 161/162 are generally oriented perpendicular to the LA1. The slots are shaped and sized so that they will engage with expansion member 140 as it is moved in the proximal direction. In some embodiments, moving the expansion member 140 into the first slot 161 increases the height of the proximal end a first distance and moving the expansion member 140 into the second slot 162 increases the height of the proximal end a second distance, with the second distance being greater than the first distance. The expansion member 140 can include one or more angled portions to engage the slots 161/162. For examples, as shown in FIGS. 7A-7C, the expansion member 140 includes first angled portion 141 and second angled portion 142. In between the angled portions 141 and 142 may be a relatively flat section which can allow the expansion member 140 to "lock" into the first slot 161. A similar flat section may be located distally from the angled portion 142 so that the expansion member 140 may "lock" into the second slot 162.

In some embodiments, the expansion element 140 has a width equal to that of the openings 113, 123 in the upper portion 110 and lower portion 120. In this manner, the expansion element 140 can be sized as tall as the overall height of the implant 100, or even taller. In such embodiments, the taller expansion element is able to achieve a much greater increase in height and lordosis upon expansion of the implant.

The hinge portion 130 is generally located at the distal end of the spinal implant 100 and couples the upper portion 110 to the lower portion 120 at their distal ends 112, 122. The hinge portion can have a hinge axis which is generally aligned perpendicular to the longitudinal axis LA1 of the spinal implant 100. The hinged portion 130 allows the spinal implant to increase in height at the proximal end while remaining the same height at the distal end to thereby achieve lordosis.

Many existing cage designs cannot provide sufficient strength for a posterior spinal fusion cage of appropriate size if manufactured from PEEK. The upper and lower portions of spinal implant disclosed herein incorporate a "living hinge" design, which allows bending within the hinge region via deformation of the material. In previously known implants using PEEK, it has been very difficult to find an appropriate balance where the hinge provides sufficient flexibility to accommodate the desired range of expansion (ideally in the 5°-30° range, with a design goal of obtaining at least 15° of expansion or lordosis), while also providing enough strength and stiffness to meet the strength requirements for the device. In particular, it has been difficult to provide a hinge design that accommodates the necessary amount of expansion while also providing an implant that is strong and stiff enough in compression-shear loading of the implant, and that also works in a range of implant heights ranging at least from 8 mm to 14 mm in height and preferably over an even wider range of heights. Hinge designs that worked for a short implant (such as 7-8 mm tall) may not work for a tall implant (such as 12-14 mm tall). Some designs worked in the short implant but did not provide enough flexibility in a taller implant and resulted in breakage at the hinge. Other designs worked in the short implant and provided enough flexibility for expansion in the taller heights, but resulted in much lower shear strength or stiffness in the taller heights. The implant disclosed herein solves this problem by adopting grooves as described below.

In some embodiments, hinged portion 130 includes an elongate groove 131 on both the upper and lower portion of the implant. The elongate groove 131 is formed in the outer surfaces of the spinal implant. As described in greater detail below, the elongate groove 131 can provide the benefit of sufficient flexibility, strength, and stiffness.

The preferred implant material for the fusion cages 100 is PEEK polymer. In addition to being biocompatible, PEEK provides desired imaging characteristics post implantation. In some embodiments, the upper portion 110, lower portion 120, and hinged portion are integrally formed from a biocompatible plastic material such as PEEK.

Figure 3C:
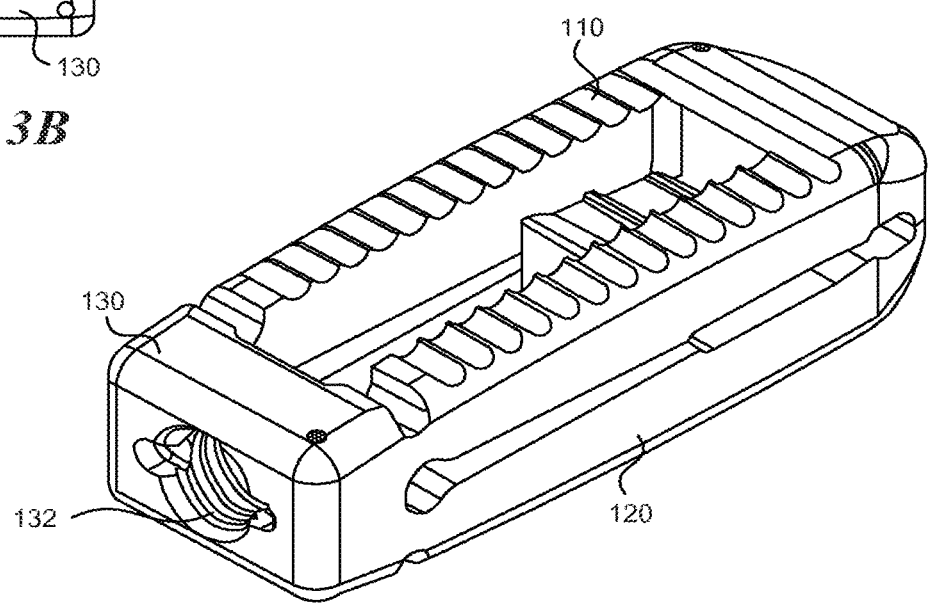
Figure 4A:
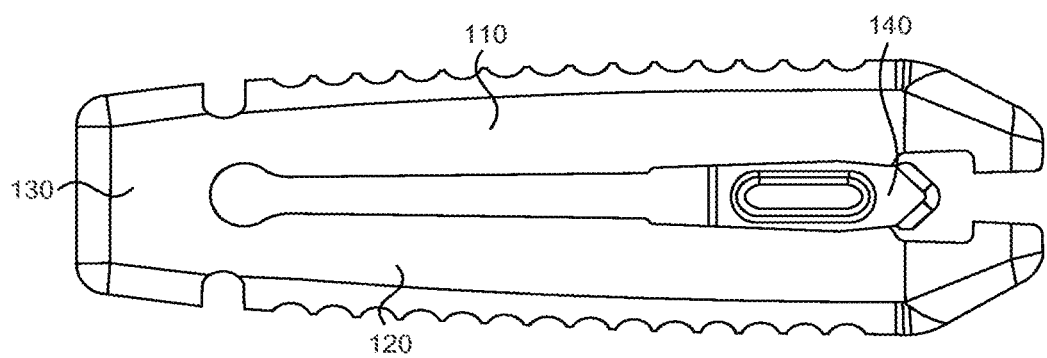
FIGS. 4A-4C are a side, side cross-sectional, and top view, respectively, of an expandable cage according to various embodiments described herein.
Figure 4B:
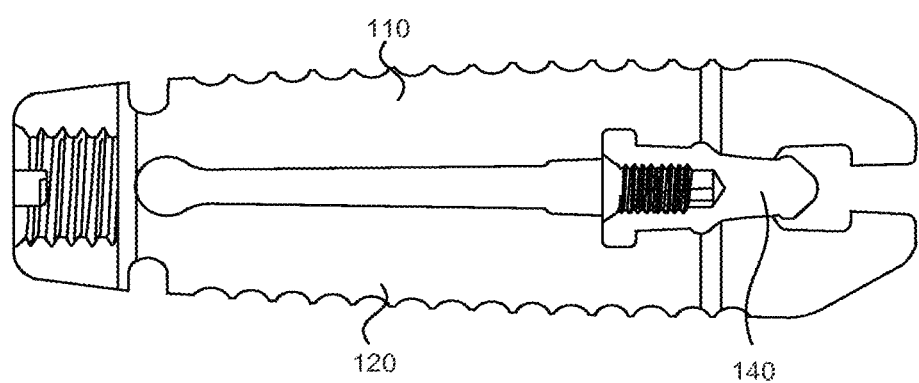
Figure 4C:
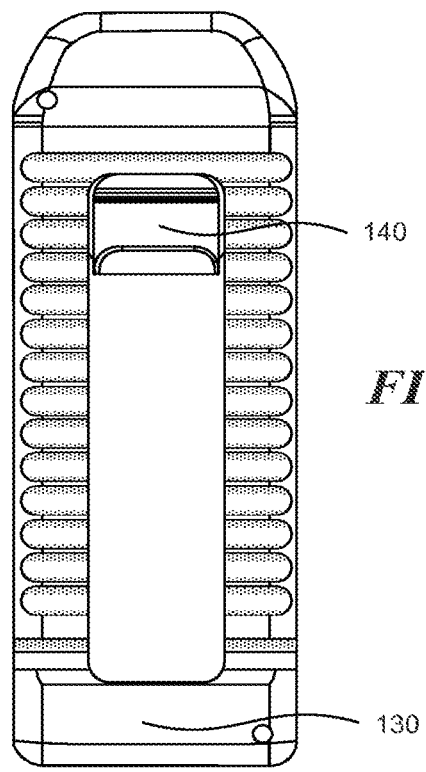
Figure 5B:
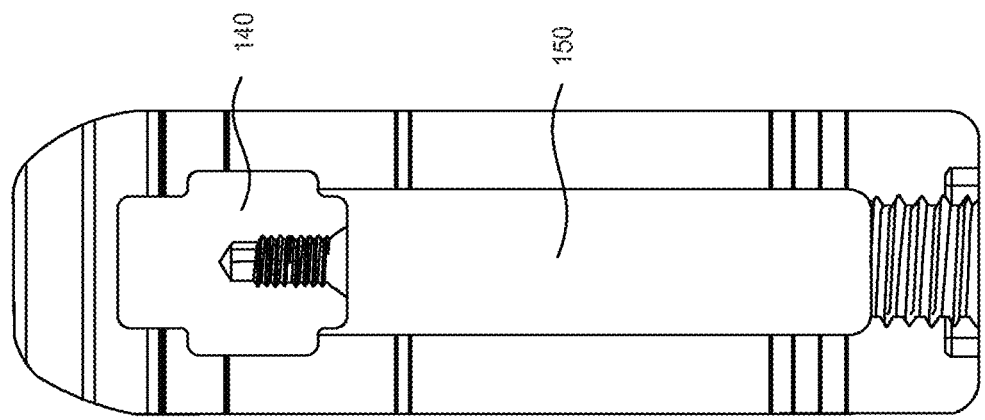
FIGS. 5A and 5B are partially see-through top views of an expandable fusion cage according to various embodiments described herein.
Figure 5A:
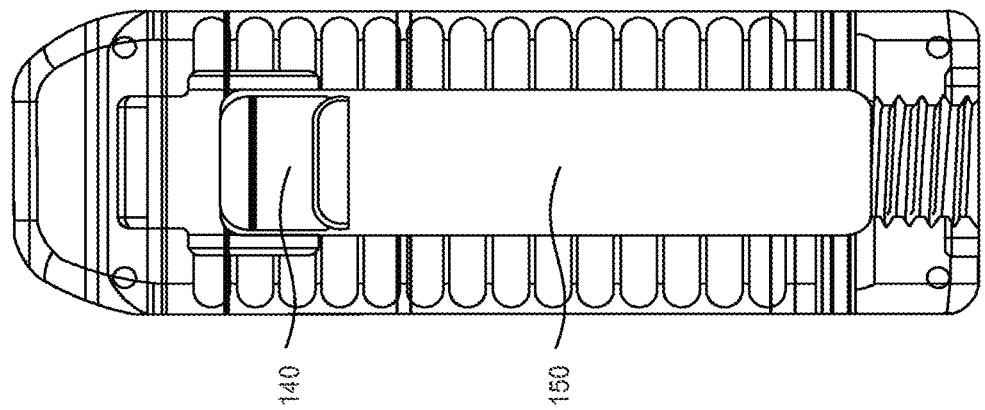
Figure 6A:
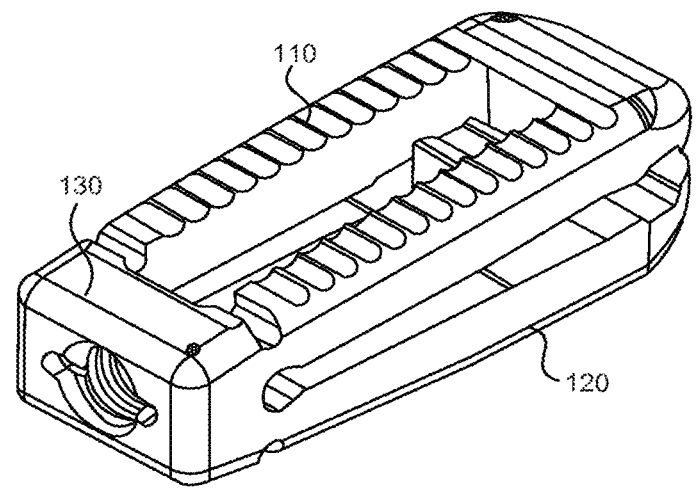
FIGS. 6A-6C are perspective, perspective see-through, and perspective cross sectional views, respectively, of an expandable fusion cage according to various embodiments described herein.
Figure 6B:
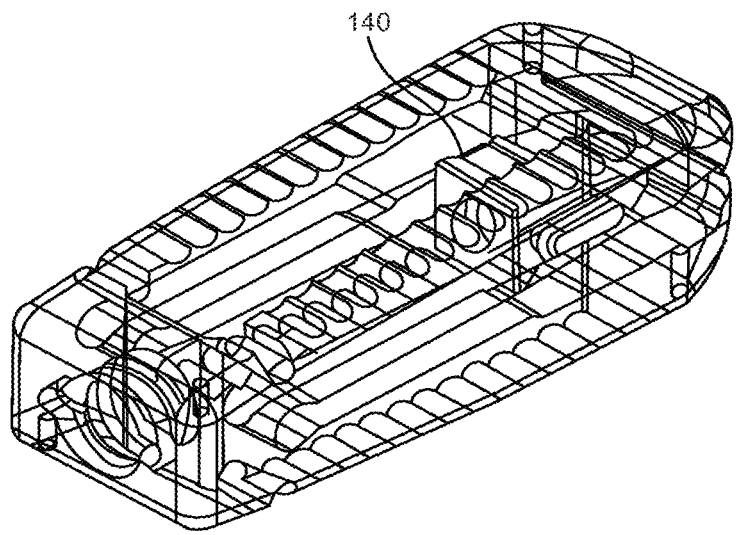
Figure 6C:
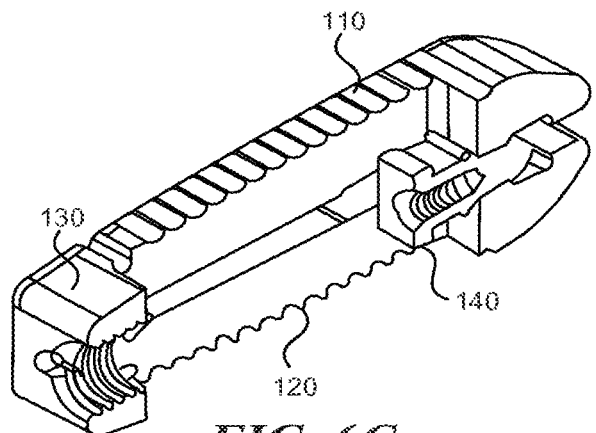

As shown in, for example, FIGS. 3A and 3C, the expansion member 140 may include a threaded recess 142. An insertion tool can be inserted into the threaded recess 142 in order to engage the expansion member 140 and move it in a direction towards the proximal end of the spinal implant 100. In order to access this recess 142, the hinged portion 130 can also include a threaded passage 132 through which the tool can be inserted in order to access the expansion member 140 positioned within the spinal implant 100.

As shown in the Figures, the height of the unexpanded spinal implant 100 can vary from the distal end to the proximal end. In some embodiments, the height gradually increases from the distal end before reaching a peak height near the proximal end, after which the height gradually decreases.

One popular surgical technique used for posterior interbody spinal fusion uses a relatively straight implant (as opposed to an implant that is highly curved in the axial plane), which is inserted in a straight path at an oblique trajectory across the disc space. This approach is often referred to as an oblique or OLIF technique. The typical oblique trajectory is oriented approximately thirty to forty-five degrees (30-45°) away from a straight A-P orientation (i.e., angled away from the sagittal plane). This oblique approach differs from a traditional PLIF approach in that PLIF cages are placed on a trajectory that is closer to straight A-P orientation (roughly parallel with the sagittal plane). Also, PLIF cages are usually placed bilaterally on either side of the anatomic midline, while the oblique approach more commonly uses on a single cage placed across the disc space with the posterior portion on the ipsilateral side of the spine and the anterior portion resting on the contralateral side across the anatomic midline. Most or all prior art expandable cages that provide anterior expansion of the cage to increase lordosis incorporate a hinge axis that is perpendicular to the long axis of the implant, thus at any distance along the length of the implant the two sides (medial and lateral) are raised by the same amount of increased height as the anterior end of the cage is expanded. If these implants are placed in a straight A-P orientation, then the hinge axis for changes in lordosis is parallel to the coronal plane, and expansion will give true sagittal-plane lordosis wherein both sides of the spine are distracted by the same amount. However, if these type of implants are placed with an oblique trajectory across the disc space, then the hinge axis will also be oriented at an angle from the coronal plane and thus expansion of the implant will tend to raise one side of the spine more than the other. This may introduce an imbalance to the spine that could result in an undesirable, iatrogenic coronal deformity.

Referring now to FIGS. 21A through 27, embodiments of the implant described herein can be asymmetrical for use with oblique surgical techniques. Oblique implant 200 can include a hinge axis 210 that is oriented at a non-orthogonal angle to the longitudinal axis 220 of the implant to match or generally match the oblique trajectory for insertion. For example, models that are designed to be inserted at a 35° angle from the sagittal plane (i.e., 55° from the coronal plane) have a hinge axis that is also oriented 35° away from perpendicular (in other words, the hinge axis is oriented 55° from the long axis of the implant). This ensures that when the implant 200 is placed along a 35° trajectory from the sagittal plane, that the hinge axis 210 operates in parallel with the coronal plane of the spine resulting in expansion that provides equal distraction to both sides of the spine and thus achieves proper spinal balance of the distracted segment. For example, the hinge axis 210 is disposed at an angle of between about fifteen (15) degrees and about forty (40) degrees relative to the longitudinal axes. Other features of the implant 200 are generally similar or identical to the features of the implant 100 described above.

With reference now to FIGS. 28 through 34, the expandable fusion cages described herein can be used with inserter instruments capable of both engaging the expandable cage and actuating the expansion element.

An inserter instrument 300 includes a shaft portion 310, a handle portion 320, and a trigger portion 330. A distal end 311 of the shaft portion is outfitted with a mechanism suitable for use in gripping the implant 100. Inside of the shaft portion 310 is a rod capable of moving distally and proximally through the shaft 310. In some embodiments, the trigger portion 330, when squeezed, results in the rod 350 deploying out of the distal end 311 of the shaft a certain distance. The rod is aligned with the expansion member inside of the implant 100 such that when it deploys out of the distal end 311, it engages the expansion element and moves it towards the proximal end of the implant 100 to thereby cause expansion of the implant 100 at the proximal end.

The inserter instrument 310 can also include an adjustment feature that accommodates different implant lengths while still providing consistency of travel in the expansion element. Each implant length requires a different amount of travel to actuate the expansion slider. A position gauge on the instrument is designed to measure correctly regardless of implant length. The expansion element distance is controlled to prevent over-actuation (which might result in the expansion slider being pushed out the front of the implant, if not controlled), and the instrument grip ergonomics and tactile feedback to the surgeon is not changed with differing implant lengths.

With reference now to FIGS. 35-41, another instrument that can be used with the expandable fusion cages described herein is an expandable distractor 400. The expandable distractor 300 (or trial instrument) provides an expandable tip 410 to distract and/or measure the disc space height. Prior art examples of this type of expandable instrument may incorporate an expansion mechanism that uses a sliding/rotating bar-linkage design. However, the rotating nature of these bar-linkage mechanisms creates an inherent change in mechanical advantage, becoming more powerful the further the instrument tip is expanded. Because surgeons rely heavily on tactile feedback to determine the appropriate amount of expansion (and to avoid complications such as overdistraction of surrounding soft tissues or inadvertent fracture of the vertebral endplates), it is undesirable to have the instrument's mechanical advantage ("power") change over its range of travel. The expandable distractor 400 described herein addresses this problem by incorporating a second bar-linkage mechanism that offsets the mechanical function of the tip expansion mechanism 410. When the two mechanisms are combined, the second bar-linkage mechanism compensates for the changing mechanical advantage at the tip 410, so that the cumulative mechanical advantage of the overall instrument remains constant throughout the range of travel of the expandable tip 410.

Figure 42A:
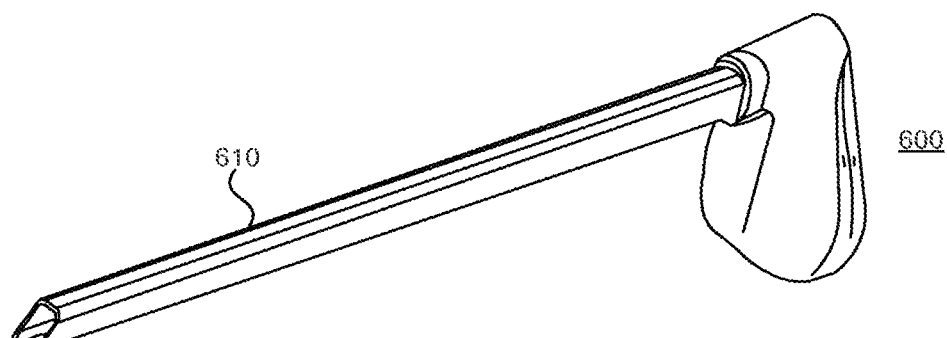
FIGS. 42A and 42B are perspective views of a bone funnel according to various embodiments described herein.
Figure 42B:
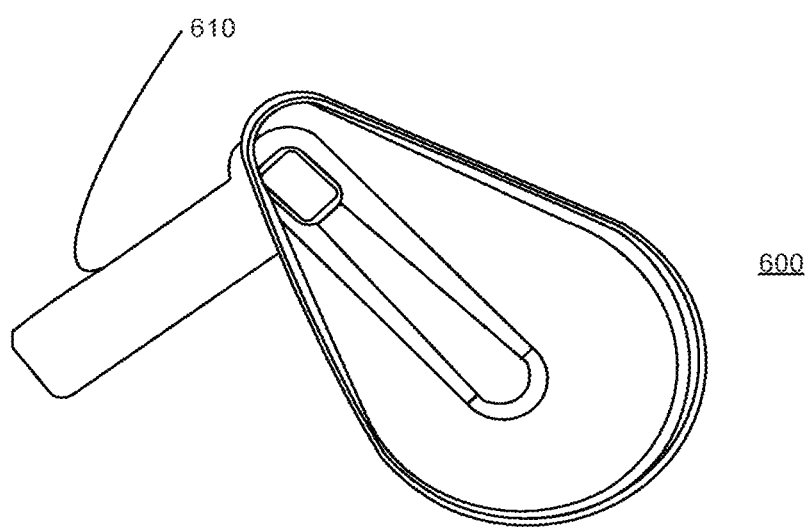
Figure 43:
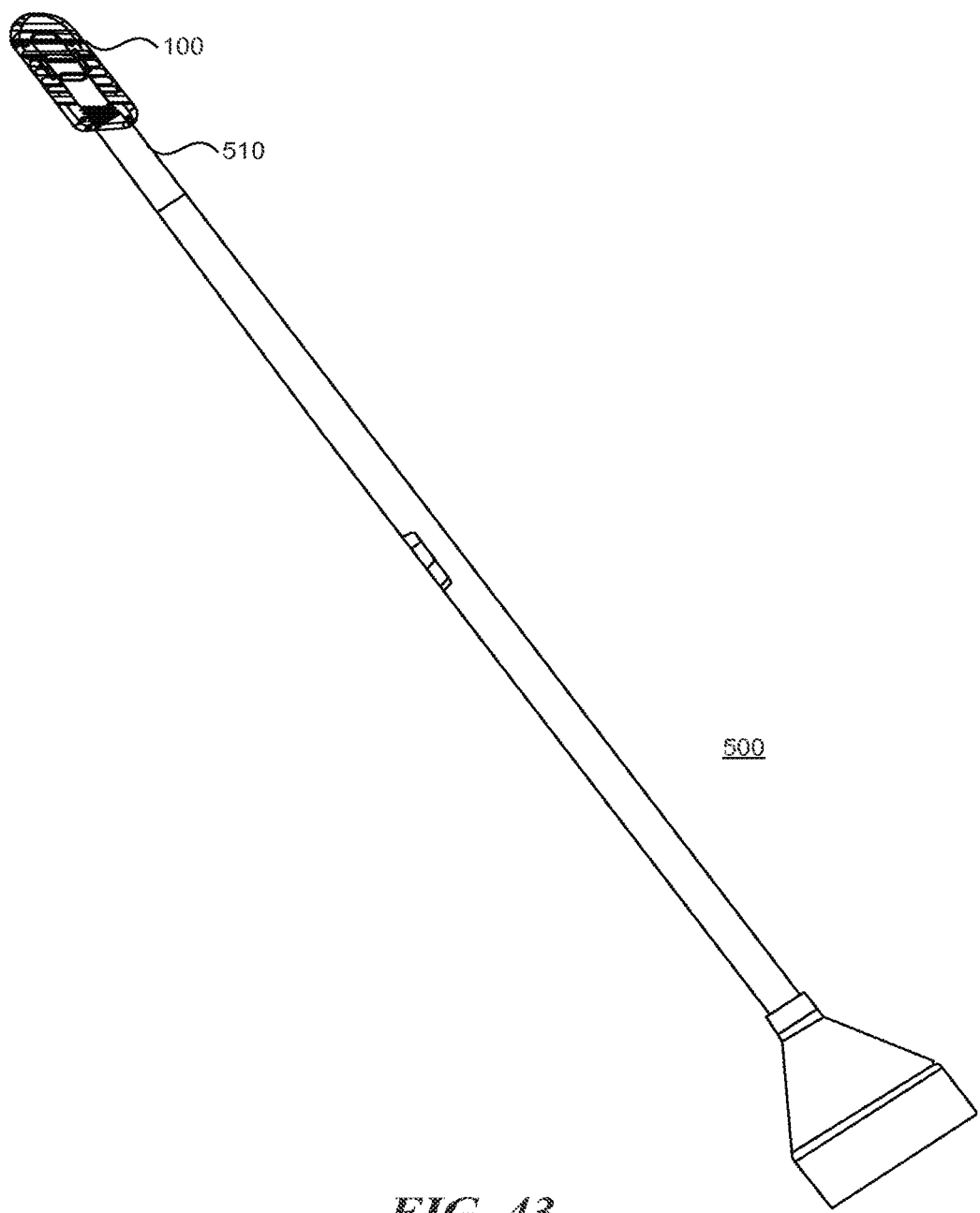
FIGS. 43 and 44 are perspective views of a bone funnel according to various embodiments described herein.
Figure 44:
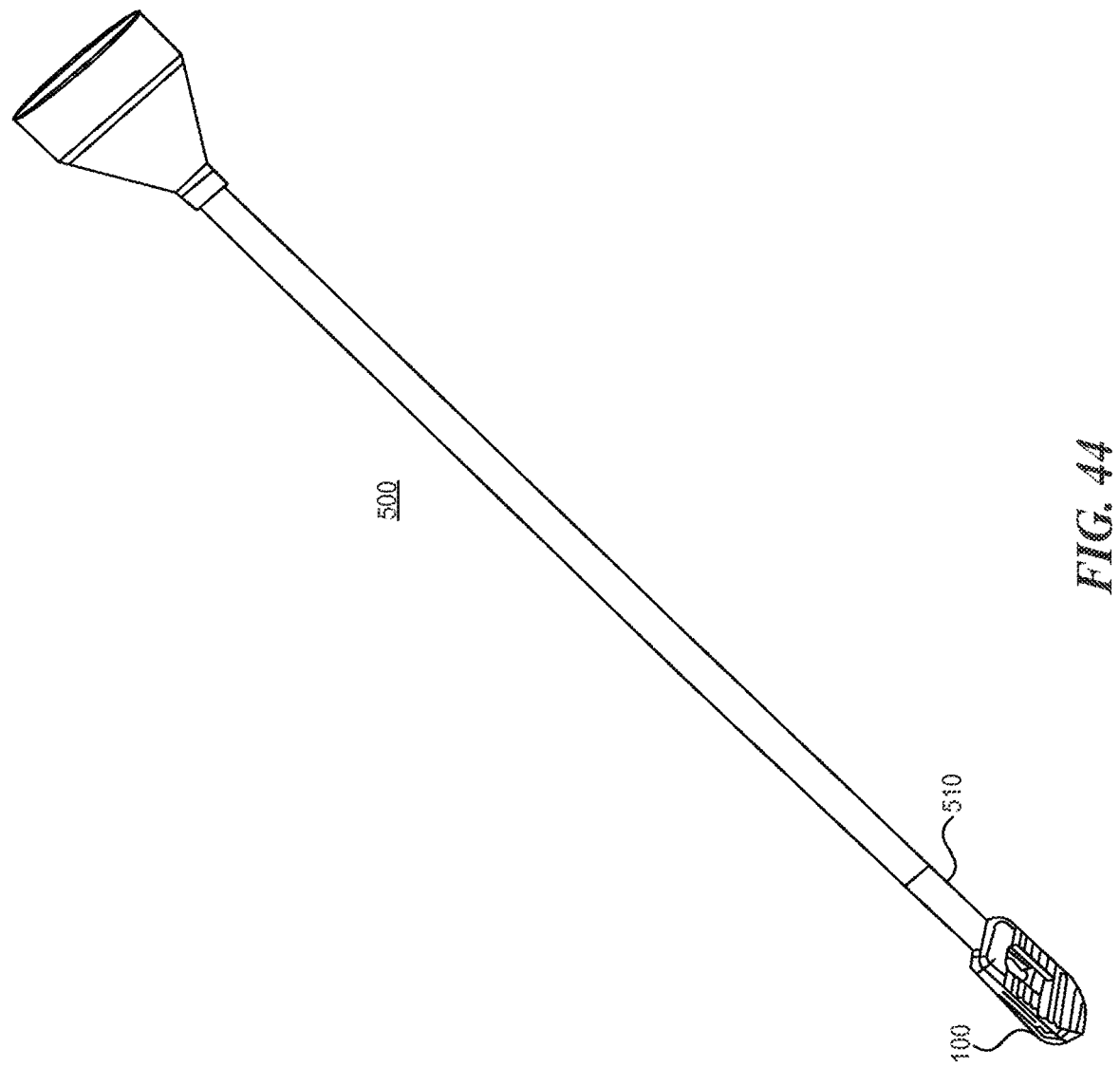

With reference now to FIGS. 42A-44, various bone funnels are disclosed for use in facilitating placement of bone graft within the disc space and within the implant. Prior art bone funnels use simple round tubes with a cup-like member on the proximal end to hold the bone graft until it is pushed through the tube into the disc space. In FIGS. 43 and 44, a bone funnel 500 having a tapered tip 510 that docks into the opening at the back of an implant 100 is shown. By docking directly onto the implant 100, this funnel 500 improves ease of use in backfilling the implant 100. Further, this funnel 500 is sized such that the opening through the bone funnel 500 is the same size as or slightly smaller than the opening at the back of the implant 100. Thus the surgeon is assured than any piece of bone graft material that is made small enough to fit down into the funnel 500 will be small enough to fit through the back of the implant 100.

With reference to FIGS. 42A and 42B, a bone funnel 600 that uses a tube 610 with a flattened shape rather than the typical round tube is shown. The flattened shape allows the cross-sectional area of the tube 610 to be maximized (to maximize the size and amount of bone graft materials that can fit down through the tube 610) while maintaining the height and width of the tube cross-section equal or smaller than the cross-section of the smallest implant (thus ensuring that the bone grafting step does not require a larger window of access to the disc space than is required for the implant, or cause over-distraction of the spine).

The various embodiments disclosed herein may offer one or more of the following advantages:

The oblique implants can provide true sagittal-plane lordosis as the implant is expanded, despite being placed at an oblique trajectory across the disc space.

The implants can provide multiple steps of distraction. For example, the expansion element can include two seats of differing heights. When the surgeon pushes the expansion element forward until the first scat engages the locking features at the distal end of the implant, the implant is expanded by a first incremental height, and the mating locking features between the implant body and the expansion element seat ensure that the in situ forces on the implant will not dislodge the expansion element from that location (thus preventing collapse of the expanded implant). If the surgeon desires more expansion, the expansion element is advanced further until the second seat engages the locking features on the implant body. In this second expanded position, the implant is expanded to a second height that is incrementally greater than the first expanded height (because the second seat is incrementally taller than the first seat). The implant can accommodate an expansion element with 1, 2, 3 or more steps of different height, providing 1, 2, 3 or more different expanded positions, respectively.

Because of the hinge design described herein, the implants can provide a larger range of expansion. For a given disc height or angle of lordosis, the implant can achieve the necessary final expanded size with an implant that is shorter during insertion (in the unexpanded condition).

Many of the prior art designs use a screw or worm gear placed down the middle of the implant. This interferes with space for bone graft material and with cross-sectional area that can ultimately be filled with a column of fused bone between the adjacent vertebrae. Because long-term stability of the fused spine is dependent on achieving a solid bony fusion, increasing the cross-sectional area available for bony growth is desirable. Various design described herein include a relatively small expansion element rather than a screw or other component, which thereby provides a much larger area for bone graft and bony fusion.

Various implant embodiments described can allow the implant to be backfilled with bone graft material after expansion, and the open sides of the implant allow bone graft material to be extruded through the implant and out into the surrounding region within the disc space, thus filling in any gaps that may have been left and increasing the probability of a successful fusion.

Various implant embodiments described herein are much more simple than prior art devices, and can be more readily manufactured using standard materials and machining techniques resulting in a lower cost of manufacturing.

Various embodiments of the inserter instruments described herein provide the necessary function and safety limits on actuation within a single instrument, compared to prior art systems that require multiple instruments to achieve the same result and may not provide the same level of safety checks on implant expansion.

Various embodiments of the expandable distractor/trial instrument described herein provide a constant ratio of input force or torque versus expansion force on the adjacent vertebrae, as the tip is expanded. Compared with prior art expandable instrument tips that provide progressively higher ratios of expansion force versus input force/torque, this instrument design provides an increased level of safety associated with the consistency of tactile feedback to the user.

Various embodiments of the bone funnels described herein are an improvement over the prior art. The ability of one funnel to securely dock to the implant (without the need for additional steps such as threading into the implant, which would increase fiddle factor and potentially decrease the amount of working space left after docking), which increases the ease of backfilling the expanded implant with bone graft, is a benefit over prior art systems. The flattened shape of the other funnel, to maximize the cross-sectional area for bone graft delivery while keeping the instrument profile within the minimum working channel required for implant insertion, represents an improvement over the art.

The ability to extrude bone graft through the back of the implant and out the sides into the adjacent disc space area provides a benefit over the art in terms of the likelihood of achieving a successful fusion.

The implant material can optionally be chosen to enhance osseointegration between the implant and the living bone. For example, the components could be formed with a roughened surface texture or could be porous. To encourage ingrowth, PEEK components could be coated or embedded. PEEK, titanium or any other biocompatible material may provide adequate strength.

Although the technology has been described in language that is specific to certain structures, materials, and methodological steps, it is to be understood that the invention defined in the appended claims is not necessarily limited to the specific structures, material s, and/or steps described. Rather, the specific aspects and steps are described as forms of implementing the claimed invention. Since many embodiments of the invention can be practiced without departing from the spirit and scope of the invention, the invention resides in the claims hereinafter appended. Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. Moreover, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

What is claimed is:

1. A spinal implant, comprising:
   an upper portion having a proximal end, a distal end, and a longitudinal axis extending therebetween;
   a lower portion having a proximal end, a distal end, and a longitudinal axis extending therebetween; and
   a hinge portion coupling the upper and lower portion distal ends, the hinge portion having a hinge axis disposed transverse and at a non-orthogonal angle to both the longitudinal axes of the upper and lower portions.

2. The spinal implant of claim 1, wherein the hinge axis is disposed at an angle of between about fifteen (15) degrees and about forty (40) degrees relative to the longitudinal axes.

3. The spinal implant of claim 1, further comprising:
   an expansion element disposed between the upper and lower portions, the expansion element adapted for slidable movement between the upper and lower portions.

4. The spinal implant of claim 3, wherein the expansion element has a variable height along a length of the expansion element.

5. The spinal implant of claim 3, further comprising opposing surfaces defined by a lower surface of the upper portion and an upper surface of the lower portion, wherein the opposing surfaces are adapted to engage the expansion element.

6. The spinal implant of claim 5, wherein the opposing surfaces comprise at least one slot adapted to engage the expansion element.

7. The spinal implant of claim 6, wherein the expansion element has an angled outer surface adapted to engage the at least one slot to alter an overall height of the proximal ends.

8. The spinal implant of claim 6, wherein the opposing surfaces comprise at least two slots adapted to engage the expansion element and provide at least two different overall separation amounts between the proximal ends.

9. The spinal implant of claim 1, wherein the upper and lower portions each have an opening therethrough, and wherein the openings in the upper and lower portions are aligned.

10. The spinal implant of claim 1, wherein the upper portion, lower portion and hinge portion are integrally formed from a biocompatible plastic.

11. The spinal implant of claim 1, wherein the hinge portion comprises:
    an elongate groove formed in an outer surface of the upper and lower portions adjacent to the proximal ends.

12. The spinal implant of claim 1, wherein the hinge axis transverse angle generally corresponds to a desired implant implantation angle.

13. The spinal implant of claim 1, wherein the hinge axis is generally perpendicular to the sagittal plane when the implant is implanted between two adjacent vertebrae.

14. A spinal implant system, comprising:
    a spinal implant as in claim 1; and an implantation tool for positioning the implant at a desired orientation and moving an expansion element to a desired location between the upper and lower portions.

15. The spinal implant system of claim 14, further comprising:
a bone growth promoting substance disposed between the upper and lower portions.

16. The spinal implant system of claim 14, further comprising:
a funnel member for inserting a bone growth promoting substance in the implant.

17. A method of using a spinal implant, comprising:
providing a spinal implant as in claim 1, inserting the implant between two adjacent vertebra at a desired angular orientation; and
providing a desired lordotic angle of the implant between the vertebra.

18. The method of claim 17, wherein the spinal implant further comprises:
an expansion element disposed between the upper and lower portions, the expansion element adapted for slidable movement between the upper and lower portions.

19. The method of claim 18, wherein providing a desired lordotic angle of the implant between the vertebra comprises:
moving the expansion element to a desired position within the spinal implant.

20. The method of claim 17, wherein the desired angle is transverse to the anterior-posterior axis of the vertebrae, and wherein the desired lordotic angle is parallel to the anterior-posterior axis of the vertebrae.

* * * * *